United States Patent
Matsuda

(10) Patent No.: US 11,272,899 B2
(45) Date of Patent: Mar. 15, 2022

(54) IMAGING CONTROL DEVICE, METHOD FOR OPERATING IMAGING CONTROL DEVICE, PROGRAM FOR OPERATING IMAGING CONTROL DEVICE, AND RADIOGRAPHY APPARATUS

(71) Applicant: FUJIFILM CORPORATION, Tokyo (JP)

(72) Inventor: Hidenori Matsuda, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 0 days.

(21) Appl. No.: 17/117,100

(22) Filed: Dec. 9, 2020

(65) Prior Publication Data

US 2021/0204901 A1 Jul. 8, 2021

(30) Foreign Application Priority Data

Jan. 8, 2020 (JP) .............................. JP2020-001242

(51) Int. Cl.
*G01N 23/04* (2018.01)
*A61B 6/00* (2006.01)
*G01T 1/17* (2006.01)

(52) U.S. Cl.
CPC ............ *A61B 6/545* (2013.01); *A61B 6/4411* (2013.01); *G01T 1/17* (2013.01); *A61B 6/4441* (2013.01); *A61B 6/542* (2013.01)

(58) Field of Classification Search
CPC ....... A61B 6/545; A61B 6/4411; A61B 6/542; A61B 6/4441; G01T 1/17
See application file for complete search history.

(56) References Cited

U.S. PATENT DOCUMENTS

2019/0046139 A1* 2/2019 Hattori .................. A61B 6/461

FOREIGN PATENT DOCUMENTS

JP 2010-269081 A 12/2010

* cited by examiner

*Primary Examiner* — Kiho Kim
(74) *Attorney, Agent, or Firm* — Solaris Intellectual Property Group, PLLC

(57) ABSTRACT

A CPU and an FPGA of the imaging control device receive first identification information and a preparation completion signal indicating that preparation for receiving radiation has been completed from a radiation detector and transmit the first identification information and irradiation conditions of the radiation associated with the first identification information to a radiation generation unit. Then, the CPU and the FPGA receive, from the radiation generation unit, second identification information copied from the first identification information by the radiation generation unit in a case in which irradiation with radiation has succeeded. Then, the CPU and the FPGA collate the first identification information and the second identification information, and determine whether or not to perform automatic brightness control, which sets a brightness level of the radiographic image to a prescribed level and updates the irradiation conditions on the basis of the radiographic image, according to a collation result.

11 Claims, 22 Drawing Sheets

IMAGING CONTROL DEVICE, METHOD FOR OPERATING IMAGING CONTROL DEVICE, PROGRAM FOR OPERATING IMAGING CONTROL DEVICE, AND RADIOGRAPHY APPARATUS

CROSS-REFERENCE TO RELATED APPLICATIONS

The present application claims priority under 35 U.S.C. § 119 to Japanese Patent Application No. 2020-001242 filed on Jan. 8, 2020. The above application is hereby expressly incorporated by reference, in its entirety, into the present application.

BACKGROUND

1. Technical Field

The technology of the present disclosure relates to an imaging control device, a method for operating the imaging control device, a program for operating the imaging control device, and a radiography apparatus.

2. Description of the Related Art

Radiographic moving image capture (hereinafter, simply referred to as moving image capture) is performed which irradiates a subject with radiation from a radiation generation unit including a radiation source and outputs a radiographic image output from a radiation detector at a predetermined frame interval. In the moving image capture, automatic brightness control (ABC) described in JP2010-269081A is performed. The automatic brightness control is control to maintain a brightness level of the radiographic image at a prescribed level.

The dose of radiation transmitted through the subject varies depending on, for example, the body thickness of the subject. Further, the performance of the radiation source changes depending on a usage environment, such as temperature, and deterioration over time. For this reason, in some cases, a radiographic image having a brightness level suitable for the set irradiation conditions is not captured. Therefore, the automatic brightness control is required.

The automatic brightness control is performed in the order of the following processes:
(1) Irradiation conditions of radiation are set in the radiation generation unit;
2) The radiation generation unit irradiates the subject with radiation on the basis of the set irradiation conditions;
(3) The radiation detector outputs a radiographic image;
(4) The radiographic image is transmitted from the radiation detector to an imaging control device;
(5) The imaging control device calculates the brightness level of the radiographic image;
(6) The calculated brightness level is compared with a prescribed level; and
(7) The irradiation conditions are updated such that the brightness level becomes the prescribed level.

The automatic brightness control is so-called feedback control which repeats the series of processes (1) to (7) in order to maintain the brightness level of the radiographic image at the prescribed level. The automatic brightness control makes it possible to maintain the brightness level of the radiographic image at the prescribed level even in a case in which the subject changes or the performance of the radiation source changes.

SUMMARY

In some cases, the radiation generation unit fails in irradiation with radiation due to, for example, the malfunction of the radiation tube that emits the radiation. In a case in which the failure in the irradiation with the radiation occurs during the moving image capture, there is a concern that the irradiation conditions will be erroneously updated on the basis of the radiographic image that is meaningless as data.

An object of the technology of the present disclosure is to provide an imaging control device, a method for operating the imaging control device, a program for operating the imaging control device, and a radiography apparatus which can suppress the execution of inappropriate automatic brightness control.

In order to achieve the above object, according to the present disclosure, there is provided an imaging control device that controls radiographic moving image capture which irradiates a subject with radiation from a radiation generation unit including a radiation source and outputs a radiographic image output from a radiation detector at a predetermined frame interval. The imaging control device comprises at least one processor. The processor receives first identification information and a preparation completion signal indicating that preparation for receiving the radiation has been completed from the radiation detector, transmits the first identification information and irradiation conditions of the radiation associated with the first identification information to the radiation generation unit, receives, from the radiation generation unit, second identification information copied from the first identification information by the radiation generation unit in a case in which the irradiation with the radiation has succeeded, collates the first identification information and the second identification information, and determines whether or not to perform automatic brightness control, which sets a brightness level of the radiographic image to a prescribed level and updates the irradiation conditions on the basis of the radiographic image, according to a collation result.

The processor may not perform the automatic brightness control in a case in which the first identification information and the second identification information are not identical to each other.

Preferably, the radiation generation unit detects actual irradiation conditions which are actual irradiation conditions of the radiation and associates the actual irradiation conditions with the second identification information. Preferably, the processor receives the actual irradiation conditions from the radiation generation unit in addition to the second identification information and updates the irradiation conditions on the basis of the actual irradiation conditions in addition to the radiographic image in a case in which the automatic brightness control is performed.

Preferably, the processor performs control to display the radiographic image at the frame interval and does not update the display of the radiographic image in a case in which the first identification information and the second identification information are not identical to each other.

Preferably, the processor receives, from the radiation detector, the radiographic image output from the radiation detector on the basis of the radiation emitted from the radiation generation unit under the irradiation conditions and third identification information which is copied from the first identification information and is associated with the radiographic image by the radiation detector, collates the first identification information and the second identification information, and collates the second identification information and the third identification information in a case in which the first identification information and the second identification information are identical to each other.

Preferably, the processor performs the automatic brightness control only in a case in which the first identification information and the second identification information are identical to each other and the second identification information and the third identification information are identical to each other.

Preferably, the processor performs control to display the radiographic image at the frame interval and updates the display of the radiographic image only in a case in which the first identification information and the second identification information are identical to each other and the second identification information and the third identification information are identical to each other.

Preferably, the imaging control device is used in a radiography apparatus including the radiation detector that is removable.

According to the present disclosure, there is provided a method for operating an imaging control device that controls radiographic moving image capture which irradiates a subject with radiation from a radiation generation unit including a radiation source and outputs a radiographic image output from a radiation detector at a predetermined frame interval. The method comprises: a first receiving step of receiving first identification information and a preparation completion signal indicating that preparation for receiving the radiation has been completed from the radiation detector; a transmitting step of transmitting the first identification information and irradiation conditions of the radiation associated with the first identification information to the radiation generation unit; a second receiving step of receiving, from the radiation generation unit, second identification information copied from the first identification information by the radiation generation unit in a case in which the irradiation with the radiation has succeeded; a collation step of collating the first identification information and the second identification information; and a determination step of determining whether or not to perform automatic brightness control, which sets a brightness level of the radiographic image to a prescribed level and updates the irradiation conditions on the basis of the radiographic image, according to a collation result.

According to the present disclosure, there is provided a program for operating an imaging control device that controls radiographic moving image capture which irradiates a subject with radiation from a radiation generation unit including a radiation source and outputs a radiographic image output from a radiation detector at a predetermined frame interval. The program causes a computer to function as: a first receiving unit that receives first identification information and a preparation completion signal indicating that preparation for receiving the radiation has been completed from the radiation detector; a transmitting unit that transmits the first identification information and irradiation conditions of the radiation associated with the first identification information to the radiation generation unit; a second receiving unit that receives, from the radiation generation unit, second identification information copied from the first identification information by the radiation generation unit in a case in which the irradiation with the radiation has succeeded; a collation unit that collates the first identification information and the second identification information; and a determination unit that determines whether or not to perform automatic brightness control, which sets a brightness level of the radiographic image to a prescribed level and updates the irradiation conditions on the basis of the radiographic image, according to a collation result.

According to the present disclosure, there is provided a radiography apparatus comprising: a radiation generation unit including a radiation source that irradiates a subject with radiation; a radiation detector that receives the radiation transmitted through the subject and outputs a radiographic image; and an imaging control device that controls radiographic moving image capture which outputs the radiographic image output from the radiation detector at a predetermined frame interval. The radiation detector transmits first identification information and a preparation completion signal indicating that preparation for receiving the radiation has been completed to the imaging control device. The imaging control device transmits the first identification information and irradiation conditions of the radiation associated with the first identification information to the radiation generation unit. The radiation generation unit transmits, to the imaging control device, second identification information copied from the first identification information in a case in which the irradiation with the radiation has succeeded. The imaging control device collates the first identification information and the second identification information, and determines whether or not to perform automatic brightness control, which sets a brightness level of the radiographic image to a prescribed level and updates the irradiation conditions on the basis of the radiographic image, according to a collation result.

According to the technology of the present disclosure, it is possible to provide an imaging control device, a method for operating the imaging control device, a program for operating the imaging control device, and a radiography apparatus which can suppress the execution of inappropriate automatic brightness control.

BRIEF DESCRIPTION OF THE DRAWINGS

Exemplary embodiments according to the technique of the present disclosure will be described in detail based on the following figures, wherein:

FIG. 13A illustrates a case in which irradiation with radiation has succeeded and FIG. 13B illustrates a case in which the irradiation with the radiation has failed;

FIG. 14A illustrating a case in which the radiographic image is correctly transmitted and FIG. 14B illustrating a case in which the radiographic image is not correctly transmitted;

FIG. 18A illustrates the case of a collation result indicating that collation is OK and FIG. 18B illustrates the case of a collation result indicating that collation is NG;

DETAILED DESCRIPTION

First Embodiment

Figure 1:
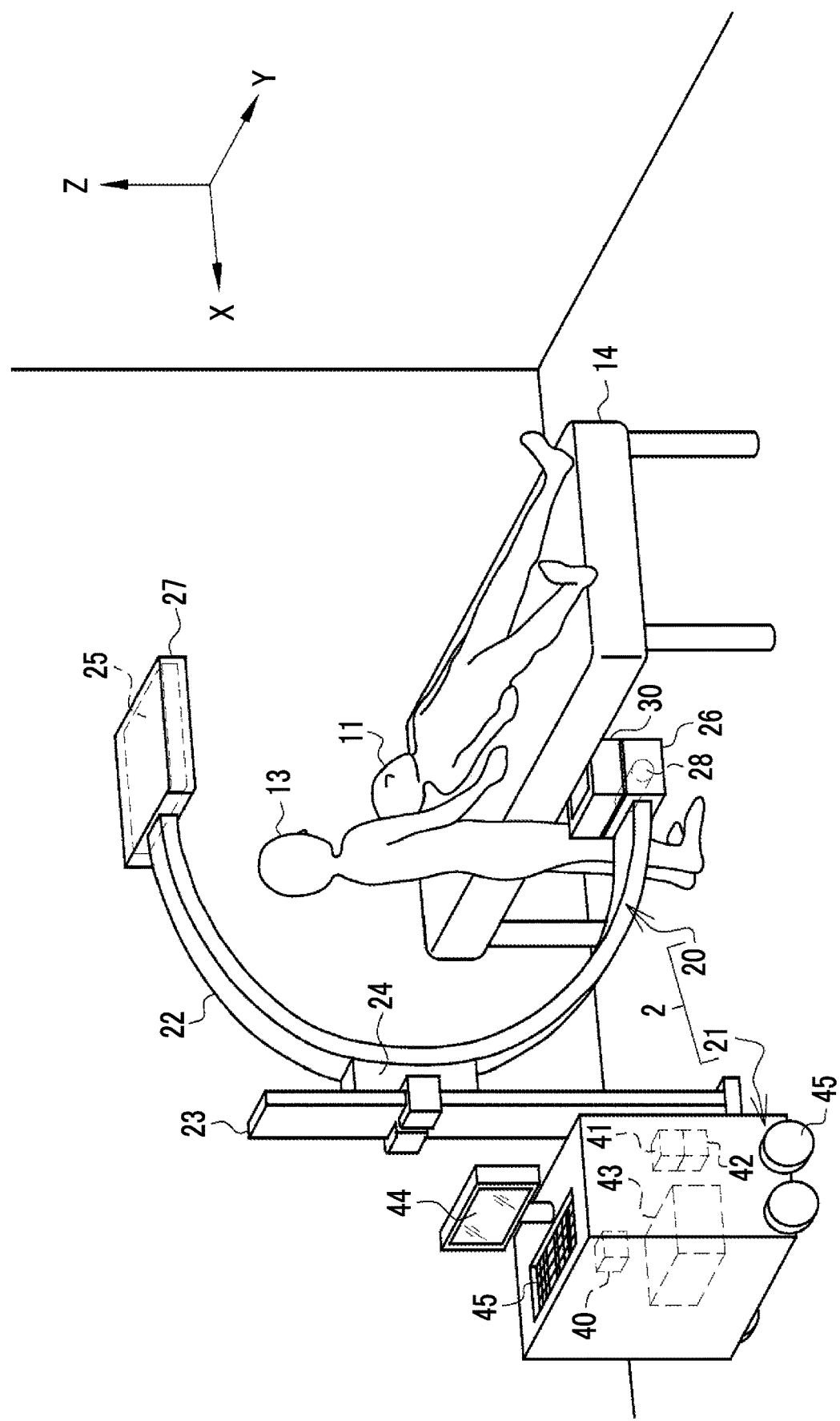
FIG. 1 is a diagram illustrating a radiography apparatus.
Figure 2:
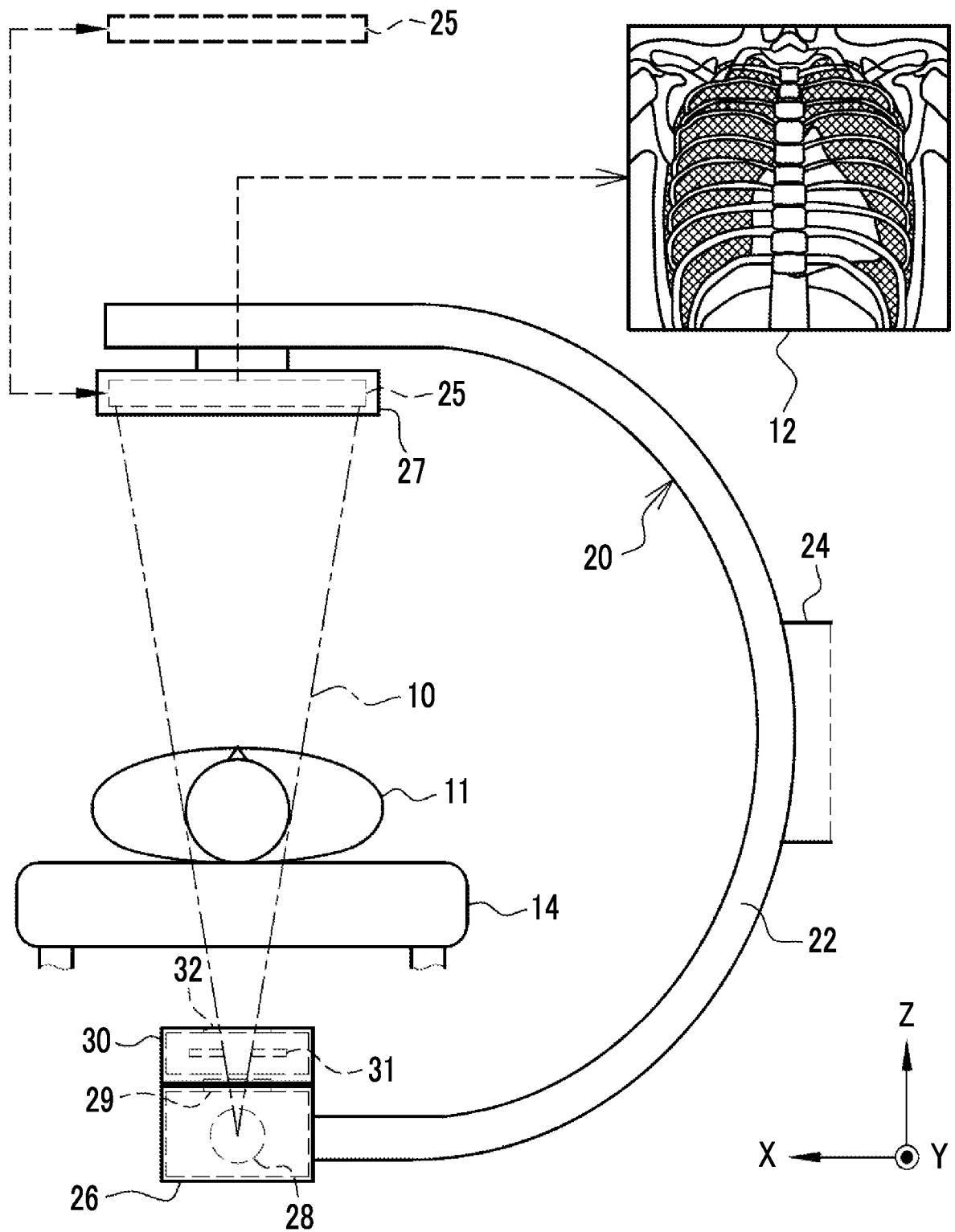
FIG. 2 is a diagram illustrating an arm portion and the like of the radiography apparatus.

In FIGS. 1 and 2, a radiography apparatus 2 irradiates a subject 11 with radiation 10, such as X-rays or γ-rays, to capture a radiographic image 12 of the subject 11. The radiography apparatus 2 can perform still image capture for capturing one radiographic image 12 and moving image capture for capturing a plurality of radiographic images 12 at a predetermined frame interval FI (see FIG. 6). The moving image capture is also called fluoroscopy. FIGS. 1 and 2 illustrate an aspect in which a radiology technician 13 takes a moving image of the chest of the subject 11 lying supine on an operating table 14 in an operating room.

The radiography apparatus 2 includes an arm portion 20 and a main body portion 21. The arm portion 20 has an arm 22 that has a substantially C-shape in a side view. The main body portion 21 has a support 23 that extends in the Z direction (height direction). The arm 22 and the support 23 are connected through a connection portion 24. The connection portion 24 makes it possible for the arm 22 to be movable in the Z direction with respect to the support 23 and makes it possible to adjust the height according to the position of the subject 11. Further, the arm 22 is rotatable about a rotation axis that passes through the connection portion 24 and extends along the X direction orthogonal to the Z direction.

A radiation detector 25 is attached to one end of the arm 22, and a radiation source 26 is attached to the other end of the arm 22. In FIGS. 1 and 2, the radiation detector 25 is located above the subject 11 and the radiation source 26 is located below the subject 11. This positional relationship is called an undertube posture. Conversely, in a case in which the radiation detector 25 is located below the subject 11 and the radiation source 26 is located above the subject 11, this positional relationship is called an overtube posture. In the undertube posture, a portion of the radiation 10 from the radiation source 26 is shielded by the operating table 14. Therefore, it is possible to reduce unnecessary exposure to the radiology technician 13 or the like around the subject 11.

The radiation detector 25 detects the radiation 10 transmitted through the subject 11 and outputs the radiographic image 12. The radiation detector 25 is accommodated in a holder 27 that is provided at the other end of the arm 22 so as to face the radiation source 26. The radiation detector 25 can be detached from the holder 27 and then used. That is, the radiation detector 25 is removable. In a case in which the radiation detector 25 is accommodated in the holder 27 and then used, it performs wire communication through, for example, a contact provided in the holder 27. On the other hand, in a case in which the radiation detector 25 is detached from the holder 27 and then used, it performs wireless communication. Therefore, the radiation detector 25 is provided with a battery (not illustrated).

A radiation tube 28 that emits the radiation 10 is accommodated in the radiation source 26. The radiation source 26 is rotatable about a rotation axis along the X direction and about a rotation axis along the Y direction orthogonal to the X direction and the Z direction such that the irradiation angle of the radiation 10 with respect to the subject 11 can be adjusted.

The radiation source 26 is provided with a rectangular radiation transmission window 29 that transmits the radiation 10. The radiation 10 emitted from the radiation tube 28 is emitted from the radiation source 26 through the radiation transmission window 29.

An irradiation field limiter 30 is attached to the radiation transmission window 29. The irradiation field limiter 30 is also called a collimator and sets the irradiation field of the radiation 10. Specifically, the irradiation field limiter 30 has a plurality of shielding plates 31 that are made of, for example, lead and shield the radiation 10 transmitted through the radiation transmission window 29. Then, the shielding plates 31 are moved to change the size of, for example, a rectangular opening defined by the shielding plates 31, thereby setting the irradiation field of the radiation 10. An irradiation opening 32 is formed in a surface of the irradiation field limiter 30 which faces the radiation transmission window 29. The radiation 10 whose irradiation field has been set by the shielding plates 31 is emitted to the subject 11 through the irradiation opening 32.

A battery 40, a voltage generator 41, an irradiation control device 42, and an imaging control device 43 are provided in the main body portion 21. A display 44 and an operation input unit 45 are provided on a top surface of the main body portion 21. A radiation generation unit 46 (see FIG. 5) is configured by the radiation source 26, the irradiation field limiter 30, the voltage generator 41, and the irradiation control device 42.

The battery 40 stores power to be supplied to each unit of the radiography apparatus 2. The battery 40 can be detached from the main body portion 21 and then charged. In a case in which the radiation detector 25 is accommodated in the holder 27, a battery of the radiation detector 25 is charged by the battery 40. The voltage generator 41 generates a tube voltage to be applied to the radiation tube 28. The radiation tube 28 and the voltage generator 41 are connected by a voltage cable (not illustrated). The tube voltage generated by the voltage generator 41 is supplied to the radiation tube 28 through the voltage cable. The irradiation control device 42 controls the irradiation with the radiation 10 by the voltage generator 41.

The imaging control device 43 controls radiography by the radiation detector 25 and the radiation source 26. In addition, the imaging control device 43 performs image processing on the radiographic image 12 output from the radiation detector 25. That is, the imaging control device 43 also has the functions of an image processing device.

The display 44 displays various screens. The various screens include an image display screen 130 (see FIG. 16) for displaying the radiographic image 12. The operation input unit 45 receives the input of various operations by the radiology technician 13 through various screens displayed on the display 44.

Four wheels 47 are attached to a lower part of the main body portion 21 in the front, rear, left, and right directions. The main body portion 21 and thus the radiography apparatus 2 can be moved in the hospital by the wheels 47.

Figure 3:
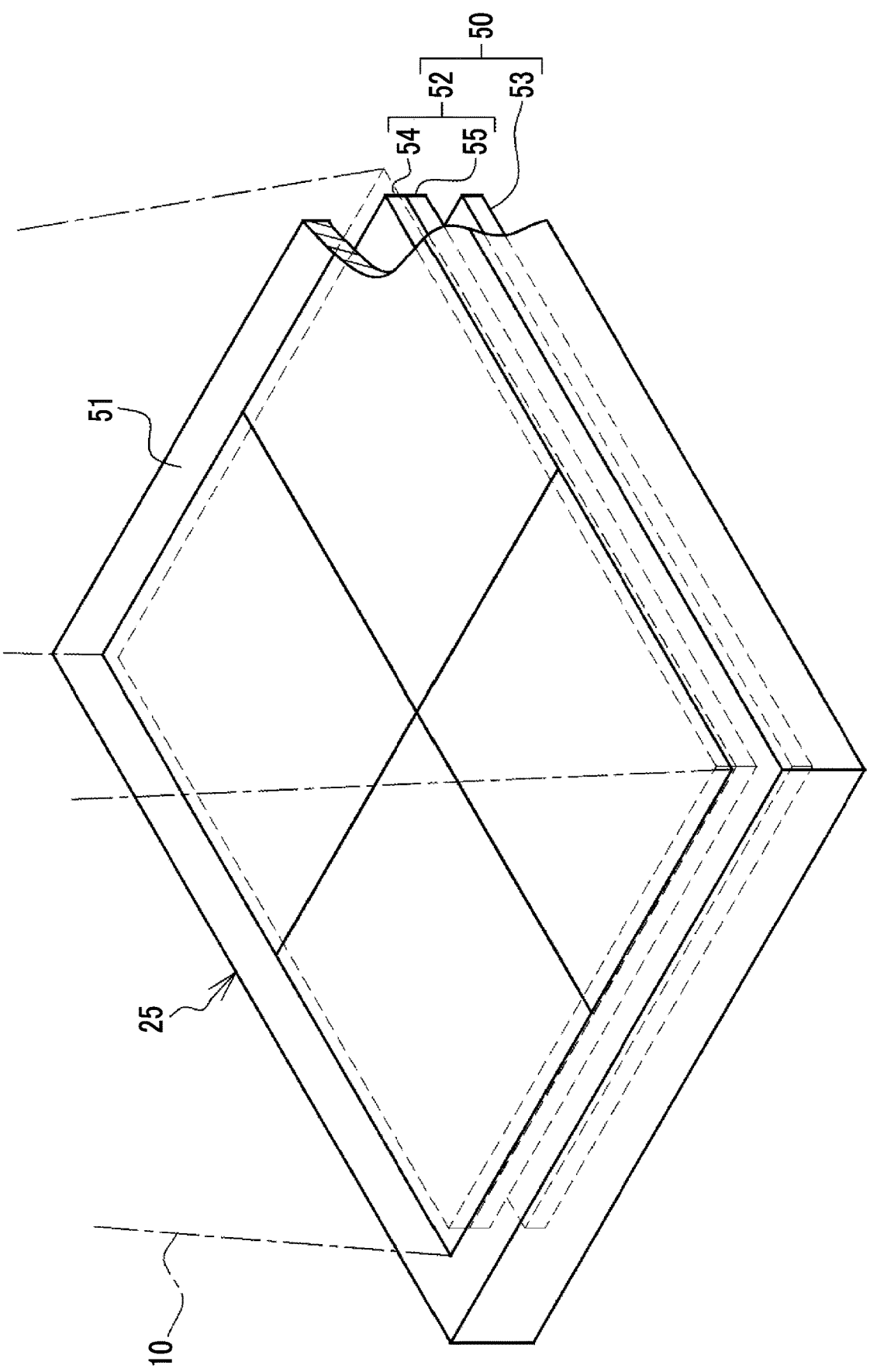
FIG. 3 is a perspective view illustrating a radiation detector.

In FIG. 3, the radiation detector 25 comprises an image output unit 50 that detects the radiation 10 transmitted through the subject 11 and outputs the radiographic image 12 represented by an electric signal and a portable housing 51 in which the image output unit 50 is accommodated. The image output unit 50 has a panel unit 52 and a circuit unit 53. The panel unit 52 includes a scintillator 54 and a light detection substrate 55. The radiation detector 25 is called a flat panel detector (FPD).

The scintillator 54 and the light detection substrate 55 are stacked in the order of the scintillator 54 and the light detection substrate 55 as viewed from the front side of the housing 51 on which the radiation 10 is incident. The scintillator 54 has a phosphor, such as CsI:Tl (thallium-activated cesium iodide) or GOS ($Gd_2O_2S$:Tb, terbium-activated gadolinium oxysulfide), converts the incident radiation 10 into visible light, and emits the visible light. The light detection substrate 55 detects the visible light emitted from the scintillator 54 and converts it into an electric signal. Specifically, the light detection substrate 55 has a plurality of pixels which are arranged in a two-dimensional matrix. As is well known, the pixel includes a photoelectric conversion unit that generates charge (electron-hole pair) using incident visible light and accumulates the charge and a switching element, such as a thin film transistor (TFT), that controls the accumulation of charge in the photoelectric conversion unit and the reading of charge from the photoelectric conversion unit.

The circuit unit 53 controls the driving of, for example, the switching elements in the light detection substrate 55. In addition, the circuit unit 53 generates a radiographic image on the basis of the electric signal output from the light detection substrate 55. Further, the scintillator 54 and the light detection substrate 55 may be stacked in the order of the light detection substrate 55 and the scintillator 54 as viewed from the front side. Furthermore, the radiation detector 25 may not be an indirect conversion type that converts the radiation 10 converted into visible light by the scintillator 54 into an electric signal as in this example, but may be a direct conversion type that directly converts the radiation 10 into an electric signal. Hereinafter, in some cases, the electric signal is referred to as a "pixel value".

Figure 4:
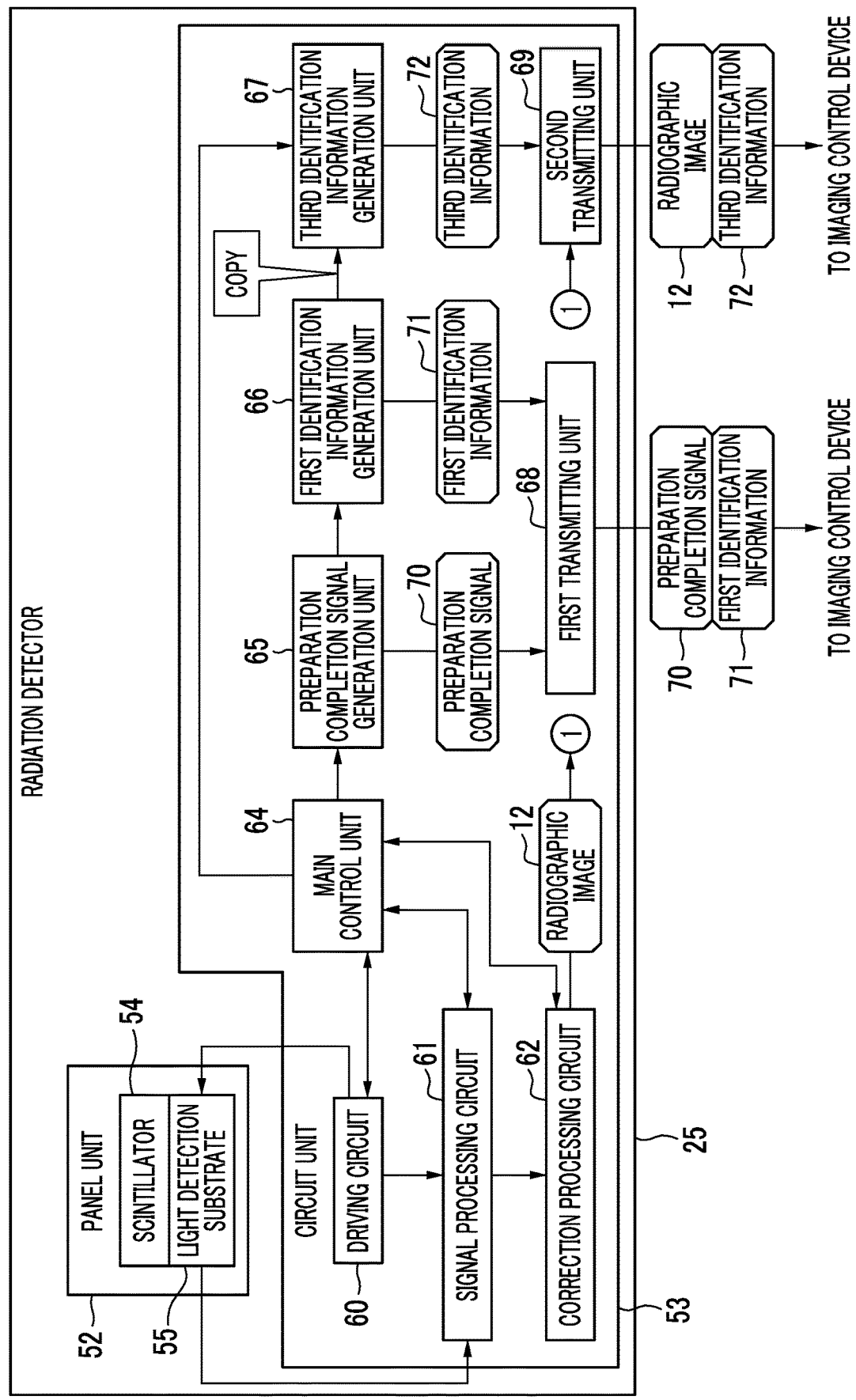
FIG. 4 is a block diagram illustrating the radiation detector.

In FIG. 4, the circuit unit 53 of the radiation detector 25 has a driving circuit 60, a signal processing circuit 61, and a correction processing circuit 62. The driving circuit 60 emits a gate pulse to each row of gate electrodes of the TFTs of each pixel in the light detection substrate 55. Therefore, a reset operation, an accumulation operation, and a reading operation are performed in the light detection substrate 55. The reset operation is an operation that reads dark charge from the photoelectric conversion unit to reset the photoelectric conversion unit. The accumulation operation is an operation that accumulates charge corresponding to the arrival dose of the radiation 10 in the photoelectric conversion unit. The reading operation is an operation that reads the charge accumulated in the photoelectric conversion unit to the signal processing circuit 61.

The signal processing circuit 61 has an integrating amplifier, a gain amplifier, a correlated double sampling (CDS) circuit, a multiplexer, and an analog-to-digital (A/D) converter (which are not illustrated).

The integrating amplifier performs a charge/electrical signal conversion process that accumulates and integrates the charge input from the photoelectric conversion unit and outputs an analog electric signal corresponding to the accumulated charge. The integrating amplifier has an amplifier reset switch. The amplifier reset switch is turned on to discard the charge accumulated in the integrating amplifier. In the reset operation, no electric signal is output from the integrating amplifier and charge is discarded. In the reading operation, after an electric signal corresponding to the charge is output from the integrating amplifier, the amplifier reset switch is turned on to discard the charge.

The gain amplifier performs an amplification process that amplifies the electric signal output from the integrating amplifier with a predetermined gain value. The CDS circuit performs a well-known correlated double sampling process on the electric signal amplified by the gain amplifier to remove a reset noise component of the integrating amplifier from the electric signal. The integrating amplifier, the gain amplifier, and the CDS circuit are provided for each column of a plurality of pixels arranged in a two-dimensional matrix.

The multiplexer sequentially selects the CDS circuits in each column one by one and serially inputs the electric signals output from each CDS circuit to the A/D converter. The A/D converter performs an A/D conversion process on the input electric signal and outputs a digital electric signal. The digital electric signal output from the A/D converter is output as the radiographic image 12 to the correction processing circuit 62.

The correction processing circuit 62 performs an offset correction process, a sensitivity correction process, and a defective pixel correction process on the radiographic image 12 from the signal processing circuit 61. The offset correction process is a process that subtracts an offset correction image detected in a state in which the radiation 10 is not emitted from the radiographic image 12 in units of pixels. The correction processing circuit 62 performs the offset correction process to remove fixed pattern noise caused by, for example, dark charge from the radiographic image 12. The sensitivity correction process is a process that corrects, for example, a variation in the sensitivity of the photoelectric conversion unit in each pixel and a variation in the output characteristics of the signal processing circuit 61 on the basis of sensitivity correction data. The defective pixel correction process is a process that linearly interpolates the value of a defective pixel with the values of surrounding normal pixels on the basis of the information of the defective pixel having an abnormal value, which is generated during shipping or a regular inspection. The correction processing circuit 62 outputs the radiographic image 12 subjected to these various processes to a second transmitting unit 69 which will be described below.

The circuit unit 53 is also provided with a main control unit 64, a preparation completion signal generation unit 65, a first identification information generation unit 66, a third identification information generation unit 67, a first transmitting unit 68, and the second transmitting unit 69. The main control unit 64 controls the overall operation of the circuit unit 53. The preparation completion signal generation unit 65 generates a preparation completion signal 70 indicating that the panel unit 52 is ready to receive the radiation 10. The preparation completion signal generation unit 65 outputs the preparation completion signal 70 to the first transmitting unit 68. A state in which the panel unit 52 is ready to receive the radiation 10 is, specifically, a state in which the light detection substrate 55 can immediately shift to the accumulation operation in accordance with the irradiation with the radiation 10. The preparation completion signal generation unit 65 is notified a state in which the panel unit 52 is ready to receive the radiation 10 through the main control unit 64.

The first identification information generation unit 66 generates first identification information 71 in synchronization with the timing when the preparation completion signal generation unit 65 generates the preparation completion signal 70. The first identification information generation unit 66 outputs the first identification information 71 to the first transmitting unit 68. The third identification information generation unit 67 generates third identification information 72 in synchronization with the timing when the correction processing circuit 62 outputs the radiographic image 12. The third identification information generation unit 67 copies the first identification information 71 and generates the third identification information 72. The third identification information generation unit 67 outputs the third identification information 72 to the second transmitting unit 69. The timing when the correction processing circuit 62 outputs the radiographic image 12 is notified to the third identification information generation unit 67 through the main control unit 64. The third identification information generation unit 67 may generate the third identification information 72 in synchronization with the timing when the first identification information generation unit 66 generates the first identification information 71.

The first transmitting unit 68 transmits the preparation completion signal 70 and the first identification information 71 to the imaging control device 43. The second transmitting unit 69 associates the radiographic image 12 with the third identification information 72. Then, the radiographic image 12 and the third identification information 72 associated with each other are transmitted to the imaging control device 43. For example, a method of registering the third identification information 72 in a file tag of the radiographic image 12 is used as a method of associating the radiographic image 12 with the third identification information 72.

The first transmitting unit 68 transmits the preparation completion signal 70 and the first identification information 71 to the imaging control device 43 before the radiation 10 is emitted. In contrast, the second transmitting unit 69 transmits the radiographic image 12 and the third identification information 72 to the imaging control device 43 after the radiation 10 is emitted. In other words, the preparation completion signal 70 and the first identification information 71, and the radiographic image 12 and the third identification information 72 are transmitted to the imaging control device 43 at different timings.

In addition, the amount of data of the radiographic image 12 and the third identification information 72 is significantly larger than the amount of data of the preparation completion signal 70 and the first identification information 71. Therefore, the time required to transmit the radiographic image 12 and the third identification information 72 is longer than the time required to transmit the preparation completion signal 70 and the first identification information 71.

Figure 5:
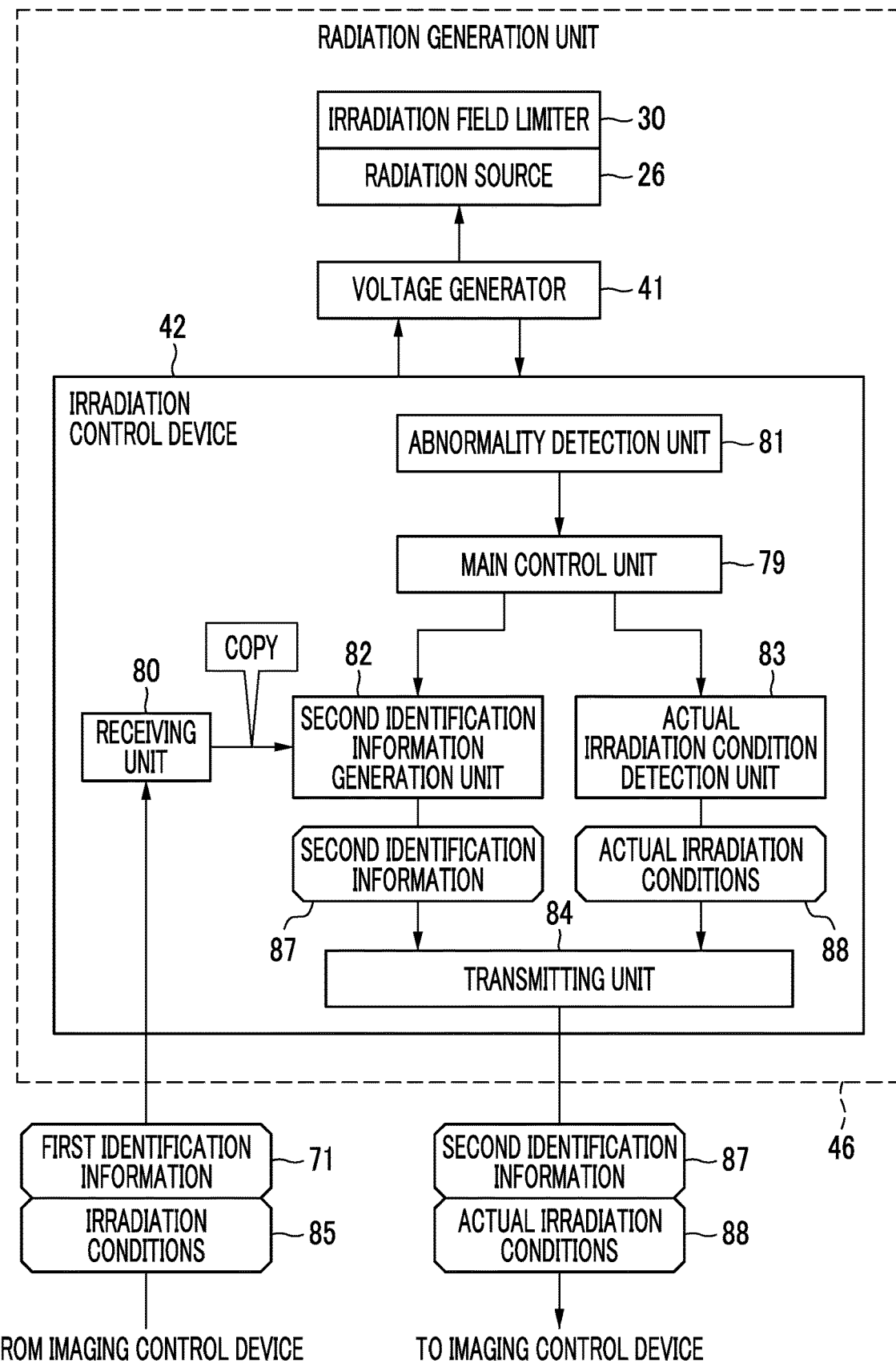
FIG. 5 is a block diagram illustrating a radiation generation unit.

In FIG. 5, the irradiation control device 42 includes a main control unit 79, a receiving unit 80, an abnormality detection unit 81, a second identification information generation unit 82, an actual irradiation condition detection unit 83, and a transmitting unit 84. The main control unit 79 controls the overall operation of the irradiation control device 42. The receiving unit 80 receives the first identification information 71 and irradiation conditions 85 from the imaging control device 43. The irradiation control device 42 transmits the irradiation conditions 85 to the voltage generator 41 to operate the radiation source 26 under the irradiation conditions 85.

Figure 6:
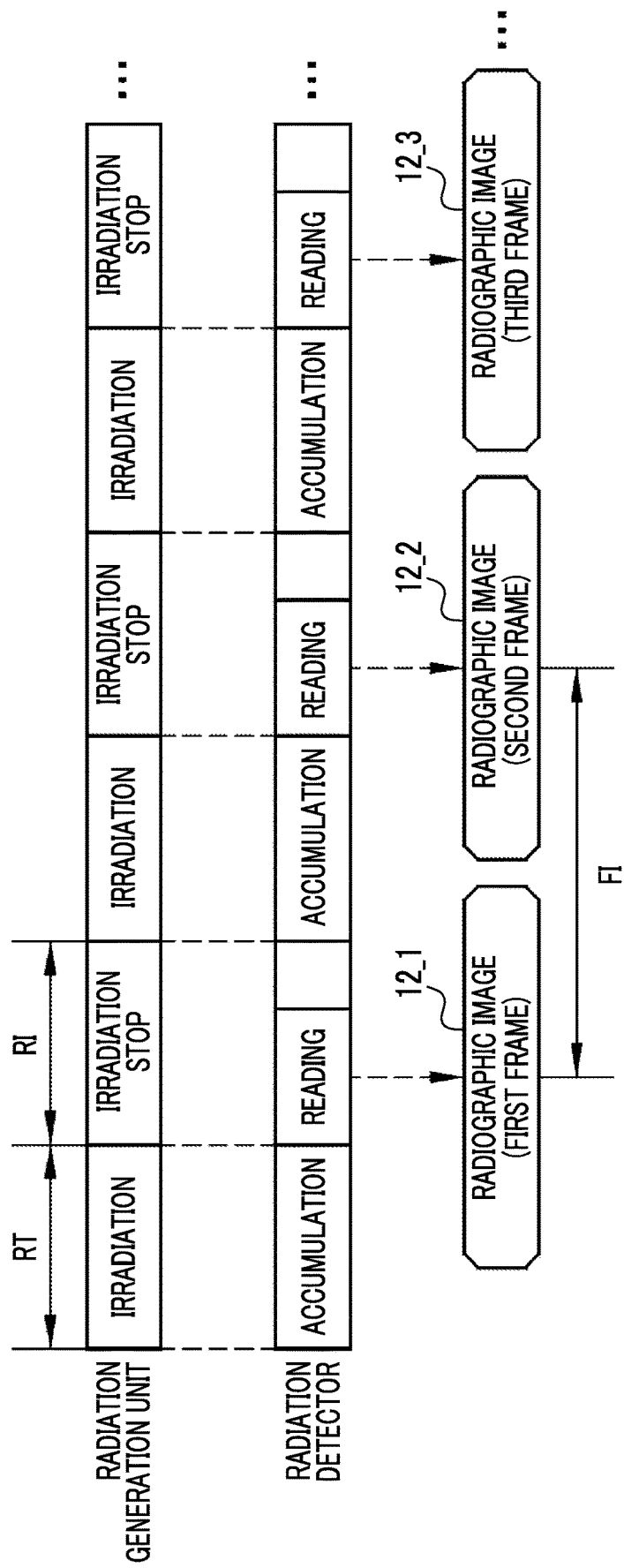
FIG. 6 is a diagram illustrating the operation timing of a radiation generation unit and the radiation detector in moving image capture.

The irradiation conditions 85 in the case of the still image capture include a tube voltage applied to the radiation tube 28, a tube current, and an irradiation time RT of the radiation 10 (see FIG. 6). The irradiation conditions 85 in the case of the moving image capture include an irradiation interval RI (see FIG. 6) of the radiation 10 in addition to the tube voltage, the tube current, and the irradiation time RT. In the case of the moving image capture, the irradiation conditions 85 are set such that the dose of the radiation 10 is less than that in the case of the still image capture. In addition, instead of the tube current and the irradiation time RT, a tube current irradiation time product may be used as the irradiation condition 85.

The abnormality detection unit 81 detects an abnormality in the radiation tube 28. For example, the abnormality detection unit 81 may detect that the radiation tube 28 is abnormal in at least one of a case in which the temperature of the radiation tube 28 is equal to or greater than a predetermined threshold value or a case in which a discharge occurs in the radiation tube 28 due to a reduction in the degree of vacuum. The radiation 10 is not emitted in a case in which the temperature of the radiation tube 28 is equal to or greater than the threshold value and in a case in which a discharge occurs in the radiation tube 28. In a case in which the abnormality detection unit 81 detects that the radiation tube 28 is abnormal, it outputs an irradiation abnormality signal indicating that the irradiation with the radiation 10 has failed to the main control unit 79. In addition, abnormalities in not only the radiation tube 28 but also the voltage generator 41 may be detected.

In a case in which the irradiation abnormality signal is not received from the abnormality detection unit 81, that is, in a case in which the irradiation with the radiation 10 has succeeded, the main control unit 79 directs the second identification information generation unit 82 to generate the second identification information 87 in synchronize with the timing when the irradiation with the radiation 10 ends. The second identification information generation unit 82 copies the first identification information 71 received by the receiving unit 80 and generates the second identification information 87. The second identification information generation unit 82 outputs the second identification information 87 to the transmitting unit 84. In contrast, in a case in which the irradiation abnormality signal is received from the abnormality detection unit 81, that is, in a case in which the irradiation with the radiation 10 has failed, the main control unit 79 does not direct the second identification information generation unit 82 to generate the second identification information 87, and the second identification information generation unit 82 does not output the second identification information 87 to the transmitting unit 84.

The actual irradiation condition detection unit 83 detects actual irradiation conditions 88. The actual irradiation conditions 88 are the irradiation conditions of the radiation 10 actually emitted by the radiation tube 28. In the case of the still image capture, the actual irradiation conditions 88 are the tube voltage, the tube current, and the irradiation time RT of the radiation 10. In the case of the moving image capture, the actual irradiation conditions 88 include the irradiation interval RI in addition to the tube voltage, the tube current, and the irradiation time RT. The tube voltage and the tube current are values that are actually measured by a voltmeter and an ammeter connected to the radiation tube 28, respectively. The irradiation time RT is a value that is actually measured by a timer which starts time measurement in a case in which a radiation detection sensor provided in the radiation source 26 or the irradiation field limiter 30 detects the radiation 10 and ends the time measurement in a case in which the radiation detection sensor does not detect the radiation. On the contrary, the irradiation interval RI is a value that is actually measured by the timer that starts time measurement in a case in which the radiation detection sensor does not detect the radiation and ends the time measurement in a case in which the radiation detection sensor detects the radiation 10.

In a case in which the irradiation abnormality signal is not received from the abnormality detection unit 81, that is, in a case in which the irradiation with the radiation 10 has succeeded, the main control unit 79 directs the actual irradiation condition detection unit 83 to detect the actual irradiation conditions 88. The actual irradiation condition detection unit 83 outputs the actual irradiation conditions 88 to the transmitting unit 84. The transmitting unit 84 associates the second identification information 87 with the actual irradiation conditions 88. Then, the second identification information 87 and the actual irradiation conditions 88 associated with each other are transmitted to the imaging control device 43. For example, a method of registering the second identification information 87 in the actual irradiation conditions 88 is used as a method of associating the second identification information 87 with the actual irradiation conditions 88.

In contrast, in a case in which the irradiation abnormality signal is received from the abnormality detection unit 81, that is, in a case in which the irradiation with the radiation 10 has failed, the main control unit 79 does not direct the actual irradiation condition detection unit 83 to detect the actual irradiation conditions 88. Therefore, the actual irradiation condition detection unit 83 does not output the actual irradiation conditions 88 to the transmitting unit 84.

As illustrated in FIG. 6, in the moving image capture, the radiation generation unit 46 emits the radiation 10 at the tube voltage, the tube current, the irradiation time RT, and the irradiation interval RI set as the irradiation conditions 85. That is, the radiation 10 is intermittently emitted a plurality of times at the predetermined irradiation interval RI. In the radiation detector 25, the accumulation operation is performed while the radiation 10 is being emitted (for the irradiation time RT). Then, the reading operation is performed at the timing when the emission of the radiation 10 ends. Therefore, a radiographic image 12_1 of a first frame, a radiographic image 12_2 of a second frame, a radiographic image 12_3 of a third frame, . . . are output at the frame interval FI. The frame interval FI is, for example, about 0.03 seconds (a frame rate of 30 frames/second). In the radiation detector 25, the reset operation is performed before the accumulation operation to remove unnecessary dark charge from the photoelectric conversion unit, which is not illustrated. In addition, an aspect may be adopted in which the radiation 10 is not intermittently emitted, but is continuously emitted, and the radiation detector 25 repeatedly performs the accumulation operation and the reading operation while the radiation 10 is continuously emitted.

Figure 7:
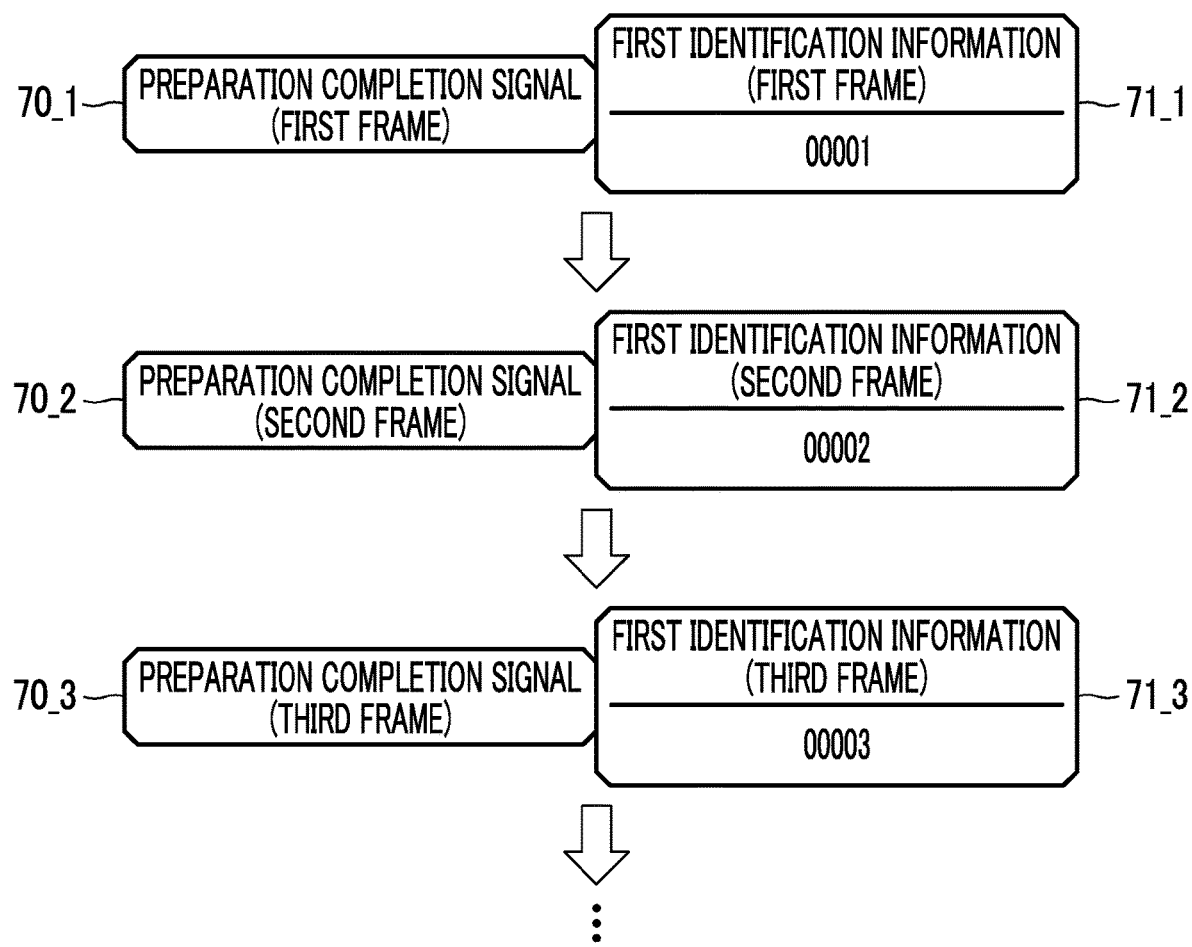
FIG. 7 is a diagram illustrating an aspect in which a preparation completion signal and first identification information are transmitted from the radiation detector to an imaging control device for each frame in the moving image capture.

As illustrated in FIG. 7, the radiation detector 25 transmits the preparation completion signal 70 and the first identification information 71 to the imaging control device 43 for each frame in the moving image capture. The first identification information 71 is, for example, a number "00001". The first identification information generation unit 66 increments the number whenever the frame in the moving image capture is changed.

Figure 8:
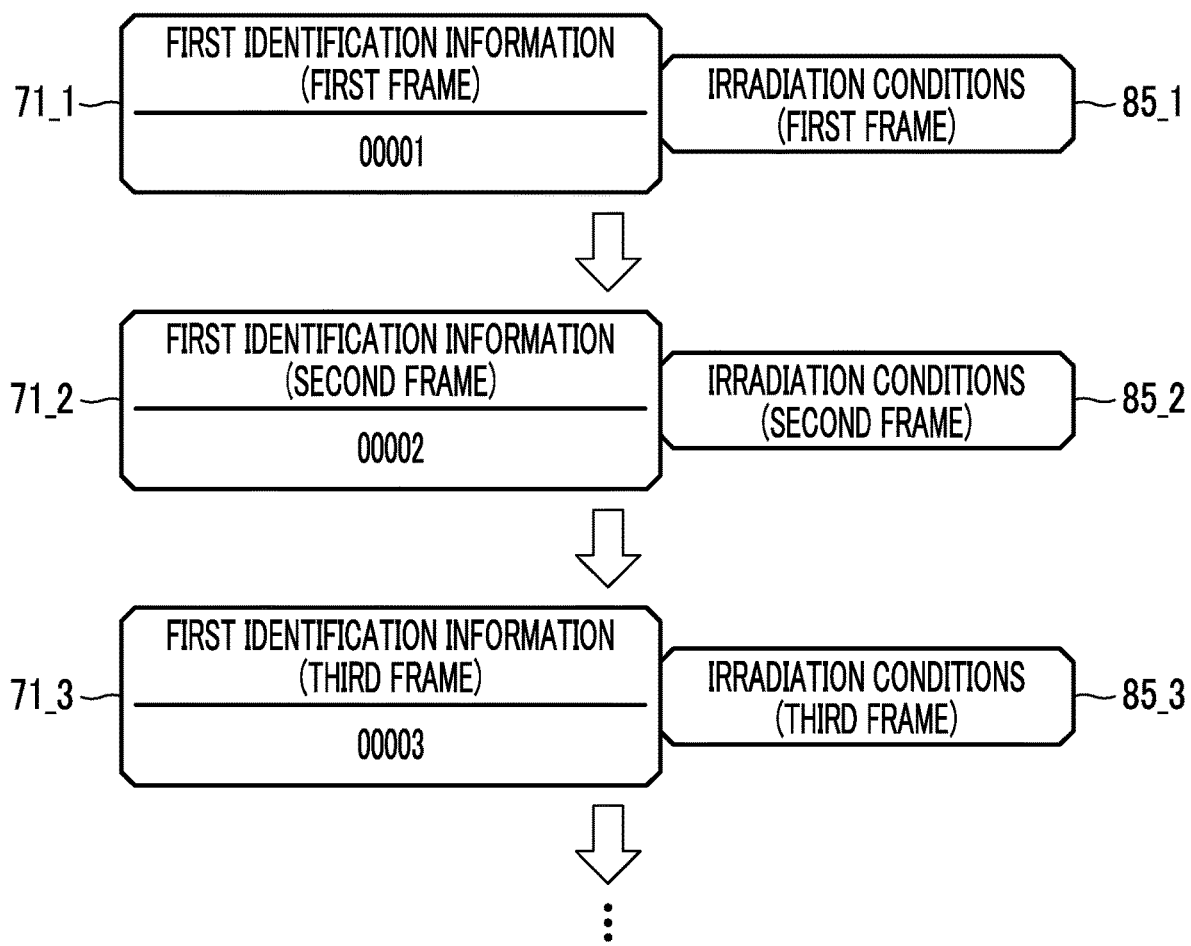
FIG. 8 is a diagram illustrating an aspect in which the first identification information and irradiation conditions are transmitted from the imaging control device to the radiation generation unit for each frame in the moving image capture.
Figure 9:
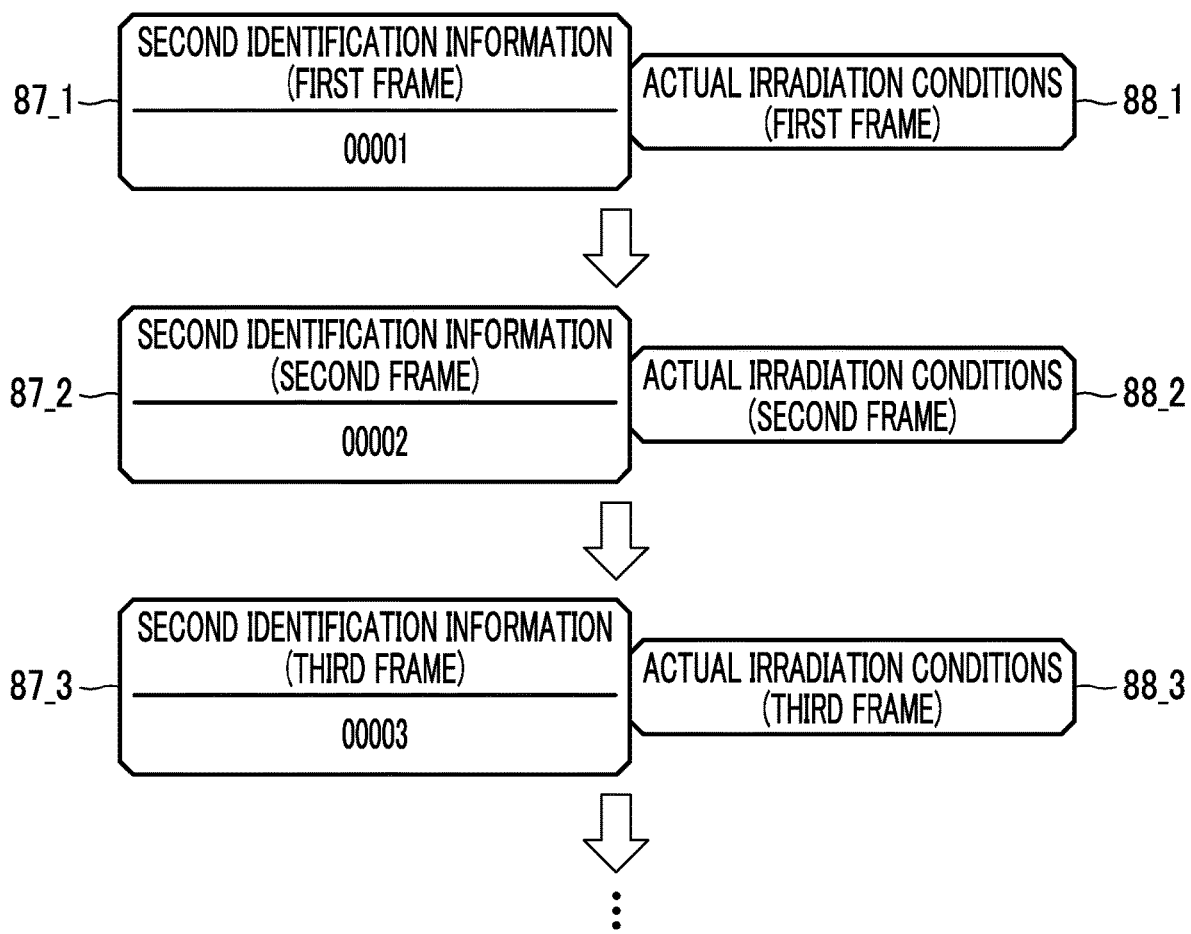
FIG. 9 is a diagram illustrating an aspect in which second identification information and actual irradiation conditions are transmitted from the radiation generation unit to the imaging control device for each frame in the moving image capture.
Figure 10:
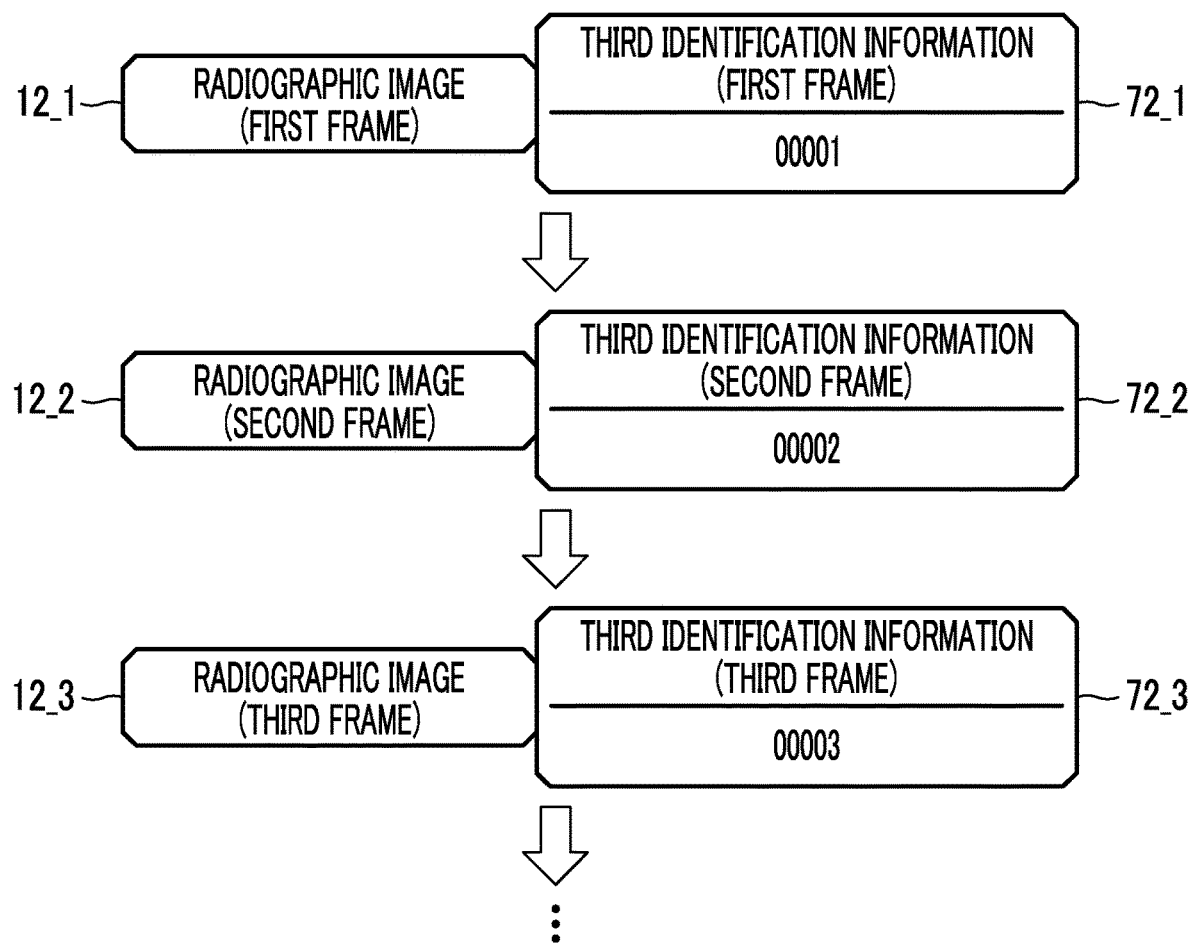
FIG. 10 is a diagram illustrating an aspect in which a radiographic image and third identification information are transmitted from the radiation detector to the imaging control device for each frame in the moving image capture.

As illustrated in FIG. 8, the imaging control device 43 transmits the first identification information 71 and the irradiation conditions 85 to the irradiation control device 42 for each frame in the moving image capture. Further, as illustrated in FIG. 9, the irradiation control device 42 transmits the second identification information 87 and the actual irradiation conditions 88 to the imaging control device 43 for each frame in the moving image capture. Further, as illustrated in FIG. 10, the radiation detector 25 transmits the radiographic image 12 and the third identification information 72 to the imaging control device 43 for each frame in the moving image capture. As such, the transmission and reception of the preparation completion signal 70 and the first identification information 71, the first identification information 71 and the irradiation conditions 85, the second identification information 87 and the actual irradiation conditions 88, and the radiographic image 12 and the third identification information 72 between the radiation detector 25 and the imaging control device 43 and between the irradiation control device 42 and the imaging control device 43 are performed for each frame in the moving image capture as long as a failure does not occur.

Figure 11:
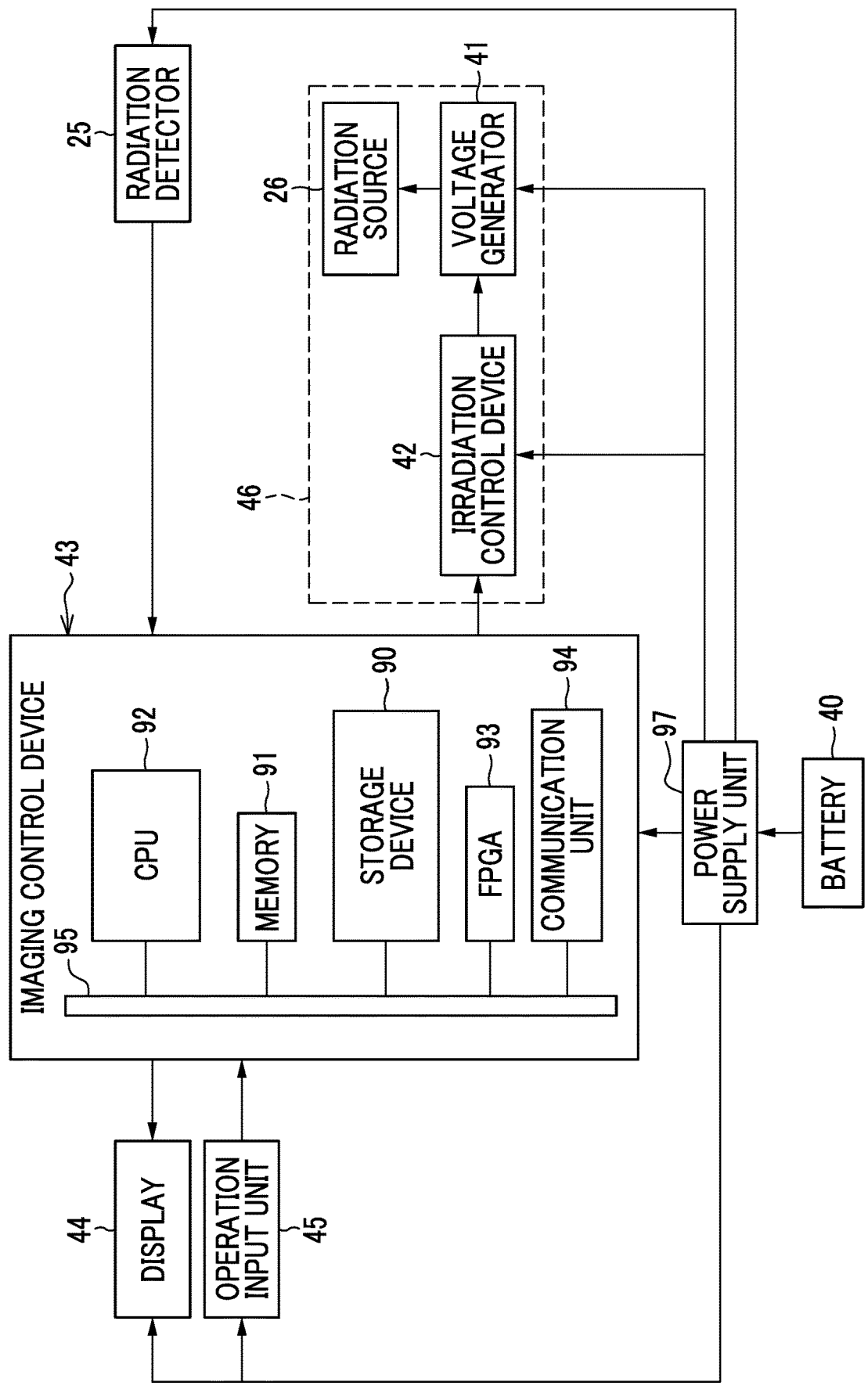
FIG. 11 is a block diagram illustrating a computer forming the imaging control device.

In FIG. 11, the computer forming the imaging control device 43 comprises a storage device 90, a memory 91, a central processing unit (CPU) 92, a field programmable gate array (FPGA) 93, and a communication unit 94. These are connected to each other through a bus line 95.

The storage device 90 is, for example, a hard disk drive that is provided in the computer forming the imaging control device 43. The storage device 90 stores, for example, a control program, such as an operating system, various application programs, and various kinds of data associated with these programs. A solid state drive may be used instead of the hard disk drive.

The memory 91 is a work memory that is used by the CPU 92 to perform processes. The CPU 92 loads the program stored in the storage device 90 to the memory 91 and performs a process corresponding to the program to control the overall operation of each unit of the computer. The CPU 92 is an example of a "processor" according to the technology of the present disclosure.

The FPGA 93 is a type of programmable logic device (PLD) in which the circuit configuration of a logic circuit can be changed after manufacturing. The FPGA 93 mainly performs image processing on the radiographic image 12 from the radiation detector 25. The FPGA 93 is also an example of the "processor" according to the technology of the present disclosure, like the CPU 92. The communication unit 94 communicates various kinds of data with, for example, the radiation detector 25 and the irradiation control device 42. A dedicated electric circuit having a dedicated circuit configuration designed to perform a specific process, such as an application specific integrated circuit (ASIC), may be used instead of the FPGA 93.

A power supply unit 97 is connected to the battery 40. The power supply unit 97 supplies power from the battery 40 to each unit of the radiography apparatus 2 including the radiation detector 25. Specifically, the power supply unit 97 includes, for example, a direct current (DC)-DC converter that converts a DC voltage from the battery 40 into a voltage having a value corresponding to a supply destination and a voltage stabilization circuit that stabilizes the value of the converted voltage.

Figure 12:
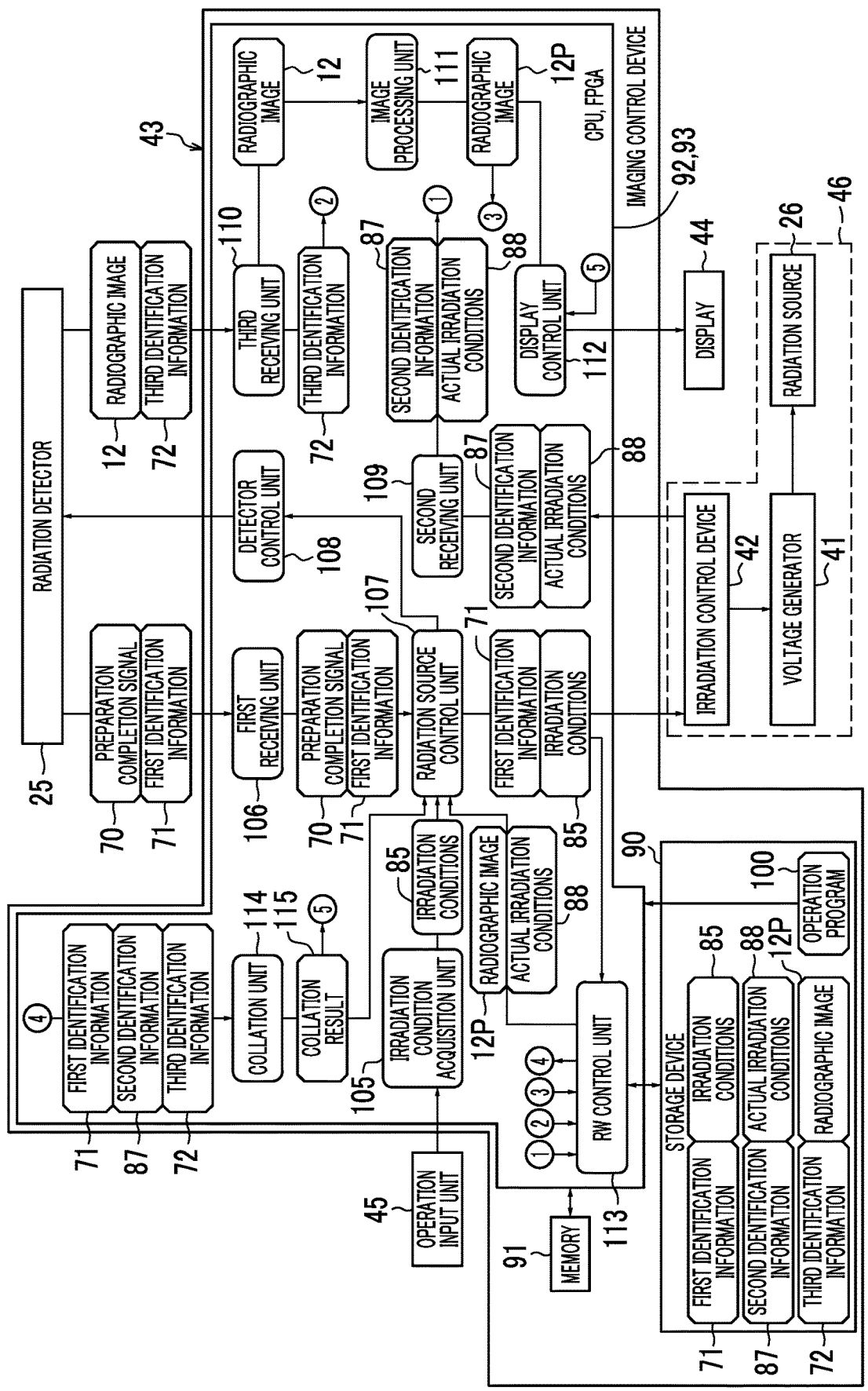
FIG. 12 is a block diagram illustrating the imaging control device.

In FIG. 12, an operation program 100 is stored in the storage device 90 of the imaging control device 43. The operation program 100 is an application program for causing the computer to function as the imaging control device 43. That is, the operation program 100 is an example of an "operation program for an imaging control device" according to the technology of the present disclosure.

In a case in which the operation program 100 is started, the CPU 92 and the FPGA 93 of the imaging control device 43 function as an irradiation condition acquisition unit 105, a first receiving unit 106, a radiation source control unit 107, a detector control unit. 108, a second receiving unit 109, a third receiving unit 110, an image processing unit 111, a display control unit 112, a read and write (hereinafter, abbreviated to RW) control unit 113, and a collation unit 114 in cooperation with, for example, the memory 91. Among the units 105 to 114, the CPU 92 takes charge of, for example, the irradiation condition acquisition unit 105, the display control unit 112, and the RW control unit 113. The FPGA 93 takes charge of the remaining units, that is, the first receiving unit 106, the radiation source control unit 107, the detector control unit 108, the second receiving unit 109, the third receiving unit 110, the image processing unit 111, and the collation unit 114.

The irradiation condition acquisition unit 105 acquires irradiation conditions 85 of the radiation 10 input by the radiology technician 13 through the operation input unit 45. The irradiation condition acquisition unit 105 outputs the irradiation conditions 85 to the radiation source control unit 107.

The first receiving unit 106 receives the preparation completion signal 70 and the first identification information 71 from the radiation detector 25. The first receiving unit 106 outputs the preparation completion signal 70 and the first identification information 71 to the radiation source control unit 107.

The radiation source control unit 107 controls the operation of the radiation source 26. The radiation source control unit 107 outputs the irradiation conditions 85 to the irradiation control device 42. In a case in which the radiology technician 13 inputs a radiography start command through an irradiation switch (not illustrated), the radiation source control unit 107 directs the radiation tube 28 to generate the radiation 10 under the set irradiation conditions 85. The radiation source control unit 107 outputs an irradiation start notification signal for notifying the start of irradiation with the radiation 10 to the detector control unit 108.

The radiation source control unit 107 associates the first identification information 71 from the first receiving unit 106 with the irradiation conditions 85. Then, the first identification information 71 and irradiation conditions 85 associated with each other are transmitted to the irradiation control device 42. For example, a method of registering the first identification information 71 in the irradiation conditions 85 is used as a method of associating the first identification information 71 with the irradiation conditions 85. Further, the radiation source control unit 107 outputs the first identification information 71 and the irradiation conditions 85 to the RW control unit 113.

The detector control unit 108 controls the operation of the radiation detector 25. The detector control unit 108 directs the radiation detector 25 to perform the accumulation operation in accordance with the irradiation start notification signal from the radiation source control unit 107. The radiation detector 25 starts the accumulation operation and performs the reading operation after the lapse of a predetermined time. Therefore, the radiographic image 12 is output from the radiation detector 25.

The second receiving unit 109 receives the second identification information 87 and the actual irradiation conditions 88 from the irradiation control device 42. The second receiving unit 109 outputs the second identification information 87 and the actual irradiation conditions 88 to the RW control unit 113.

The third receiving unit 110 receives the radiographic image 12 and the third identification information 72 from the radiation detector 25. The third receiving unit 110 outputs the radiographic image 12 to the image processing unit 111 at the frame interval FI. In addition, the third receiving unit 110 outputs the third identification information 72 to the RW control unit 113. Further, the interval at which the third receiving unit 110 outputs the radiographic image 12 to the image processing unit 111 is not limited to the frame interval FI. For example, odd-numbered frames may be thinned out and the radiographic image 12 may be output to the image processing unit 111 at a frame interval 2FI. In this case, the preparation completion signal 70 and the first identification information 71, the irradiation conditions 85, the second identification information 87 and the actual irradiation conditions 88, and the radiographic image 12 and the third identification information 72 do not need to be transmitted and received for each frame and may not be transmitted and received for the thinned-out frames.

The image processing unit 111 performs, for example, a noise suppression process, a highlighting process, and a density correction process on the radiographic image 12. The image processing unit 111 outputs a radiographic image 12P subjected to the image processing to the display control unit 112 and the RW control unit 113. In the following description, the radiographic image 12P subjected to the image processing is also referred to as the radiographic image 12 in a case in which it does not need to be particularly distinguished.

The display control unit 112 performs controls to display various screens on the display 44. For example, the display control unit 112 generates an image display screen 130 for displaying the radiographic image 12P which has been subjected to the image processing and output from the image processing unit 111 and displays the image display screen 130 on the display 44.

The RW control unit 113 controls the reading of various kinds of data from the storage device 90 and the storage of various kinds of data in the storage device 90. First, the RW control unit 113 stores the first identification information 71 and the irradiation conditions 85 from the radiation source control unit 107 in the storage device 90. In addition, the RW control unit 113 reads the first identification information 71 from the storage device 90 and outputs the first identification information 71 to the collation unit 114 whenever each frame ends. In addition, the radiation source control unit 107 may not associate the first identification information 71 with the irradiation conditions 85, but the RW control unit 113 may associate the first identification information 71 with the irradiation conditions 85 in a case in which the first identification information 71 and the irradiation conditions 85 are stored in the storage device 90.

The RW control unit 113 stores the second identification information 87 and the actual irradiation conditions 88 from the second receiving unit 109 in the storage device 90. In addition, the RW control unit 113 reads the second identification information 87 from the storage device 90 and outputs the second identification information 87 to the collation unit 114 whenever each frame ends. Further, the RW control unit 113 reads the actual irradiation conditions 88 from the storage device 90 and outputs the actual irradiation conditions 88 to the radiation source control unit 107.

The RW control unit 113 stores the third identification information 72 from the third receiving unit 110 in the storage device 90. In addition, the RW control unit 113 reads the third identification information 72 from the storage device 90 and outputs the third identification information 72 to the collation unit 114 whenever each frame ends.

The RW control unit 113 stores the radiographic image 12P subjected to the image processing from the image processing unit 111 in the storage device 90. In addition, the RW control unit 113 reads the radiographic image 12P subjected to the image processing from the storage device 90 and outputs the radiographic image 12P to the radiation source control unit 107 and the display control unit 112 whenever each frame ends.

The collation unit 114 collates the first identification information 71, the second identification information 87, and the third identification information 72. The collation unit 114 outputs a collation result 115 of the first identification information 71, the second identification information 87, and the third identification information 72 to the radiation source control unit 107 and the display control unit 112.

Figure 13A:
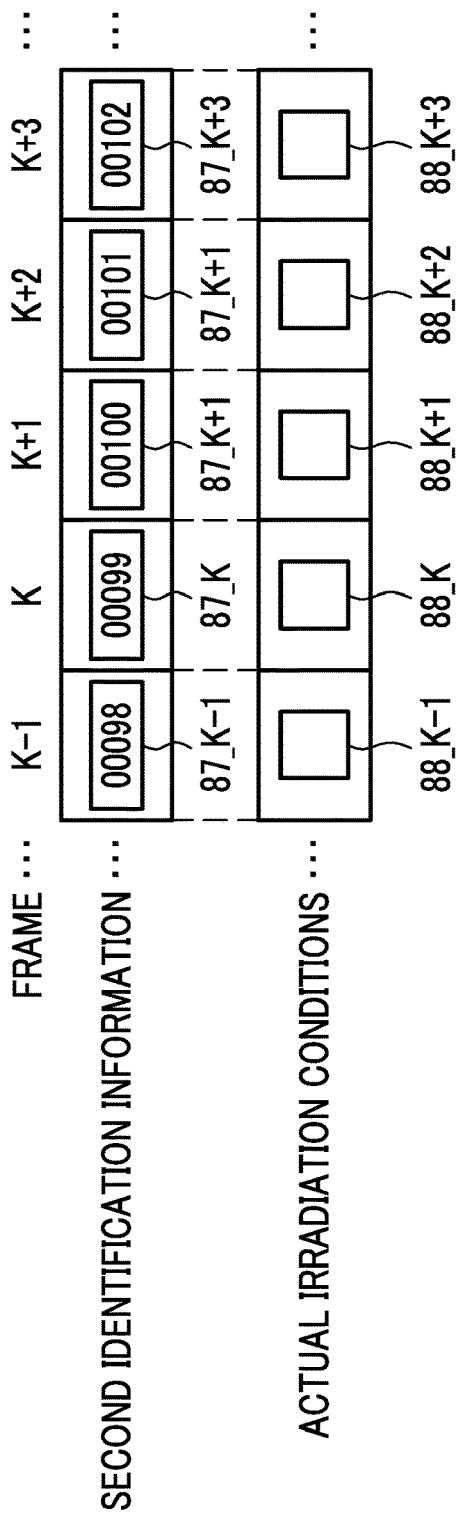
FIGS. 13A and 13B are diagrams illustrating the second identification information and the actual irradiation conditions stored in a storage device.
Figure 13B:
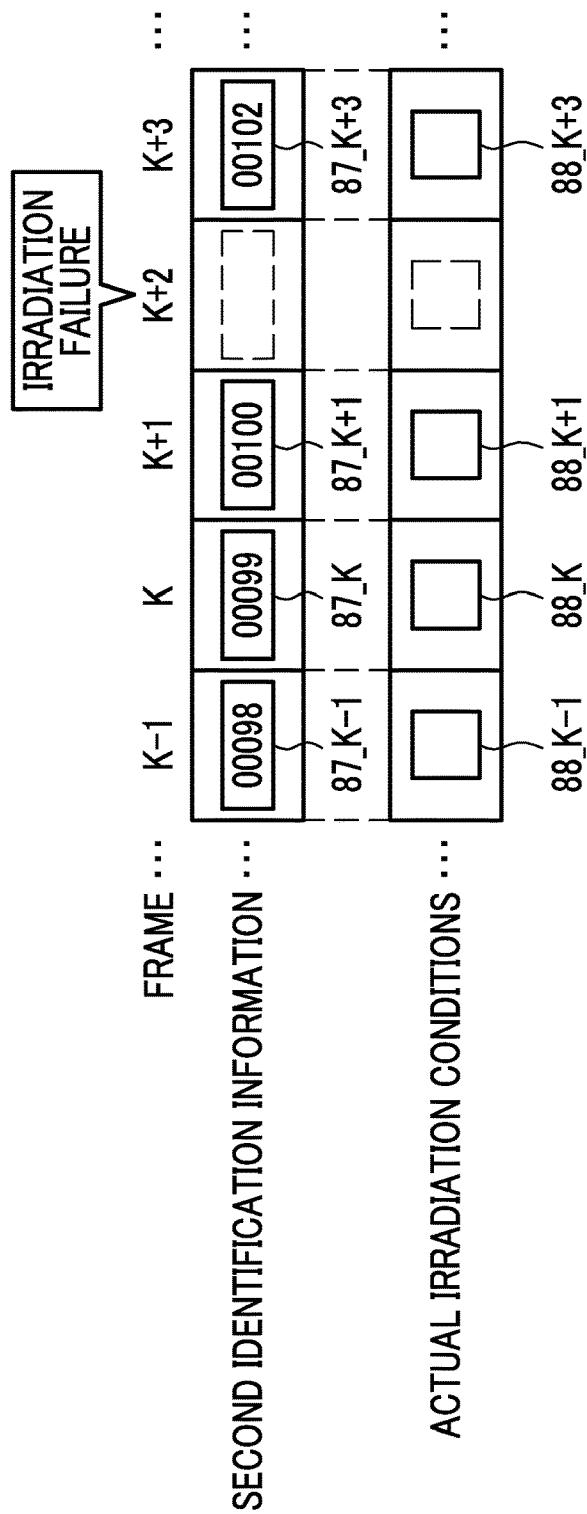

In FIGS. 13A and 13B, in a case in which the irradiation with the radiation 10 has succeeded, as illustrated in FIG. 13A, the RW control unit 113 rewrites the second identification information 87 and the actual irradiation conditions 88 in the storage device 90 as new second identification information 87 and new actual irradiation conditions 88 whenever the frame in the moving image capture is switched. In contrast, in a case in which the irradiation with the radiation 10 has failed, as illustrated in FIG. 13B, the second identification information 87 and the actual irradiation conditions 88 of the previous frame are not rewritten and are carried over to the next frame. FIG. 13B illustrates a case in which the irradiation with the radiation 10 has failed in a (K+2)-th frame (K=2, 3, 4, ..., N, N is the total number of frames) and second identification information 87_K+1 and actual irradiation conditions 88_K+1 of a (K+1)-th frame are carried over to the (K+2)-th frame.

Figure 14A:
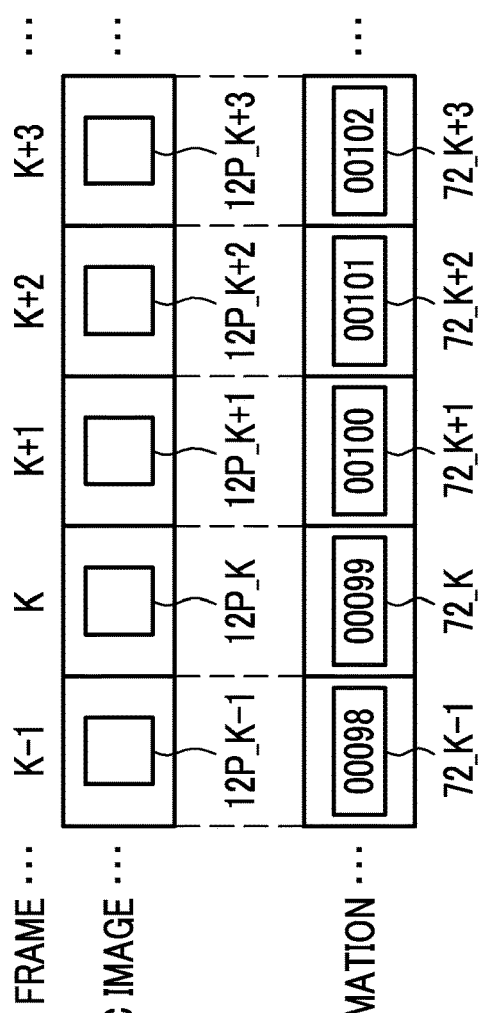
FIGS. 14A and 14B are diagrams illustrating the third identification information and the radiographic image stored in the storage device.
Figure 14B:
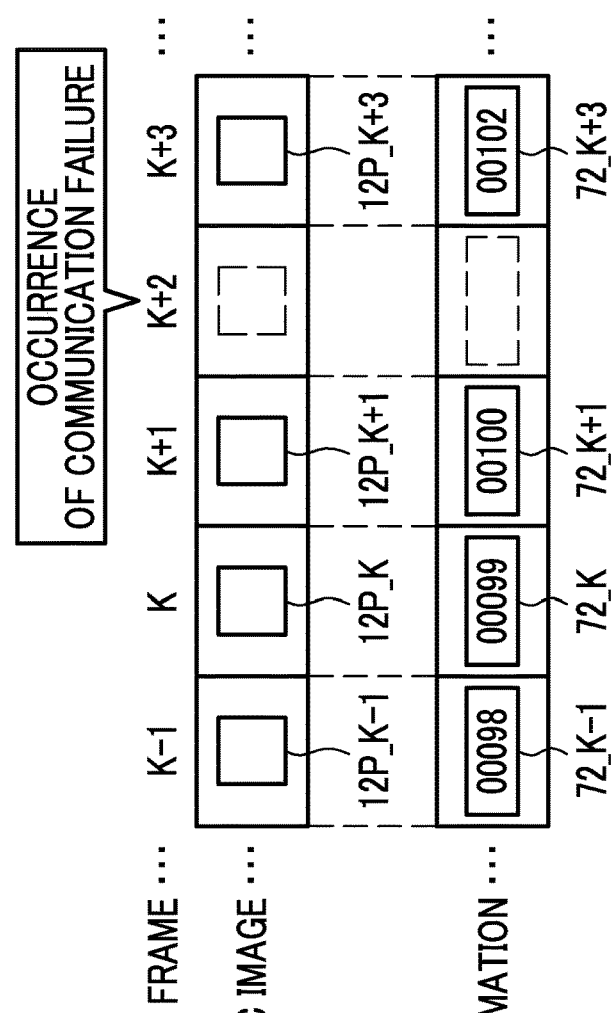

Further, in FIGS. 14A and 14B, in a case in which the radiographic image 12 is correctly transmitted from the radiation detector 25 to the imaging control device 43, as illustrated in FIG. 14A, the RW control unit 113 rewrites the radiographic image 12P and the third identification information 72 in the storage device 90 as new radiographic image 12P and new third identification information 72 whenever the frame in the moving image capture is switched. In contrast, in a case in which a communication failure occurs between the radiation detector 25 and the imaging control device 43 and the radiographic image 12 is not correctly transmitted from the radiation detector 25 to the imaging control device 43, as illustrated in FIG. 14B, the radiographic image 12P and the third identification information 72 of the previous frame are not rewritten and are carried over to the next frame. FIG. 14B illustrates a case in which the radiographic image 12 is not correctly transmitted from the radiation detector 25 to the imaging control device 43 in the (K+2)-th frame and a radiographic image 12P_K+1 and third identification information 72_K+1 of the (K+1)-th frame are carried over to the (K+2)-th frame.

Figure 15:
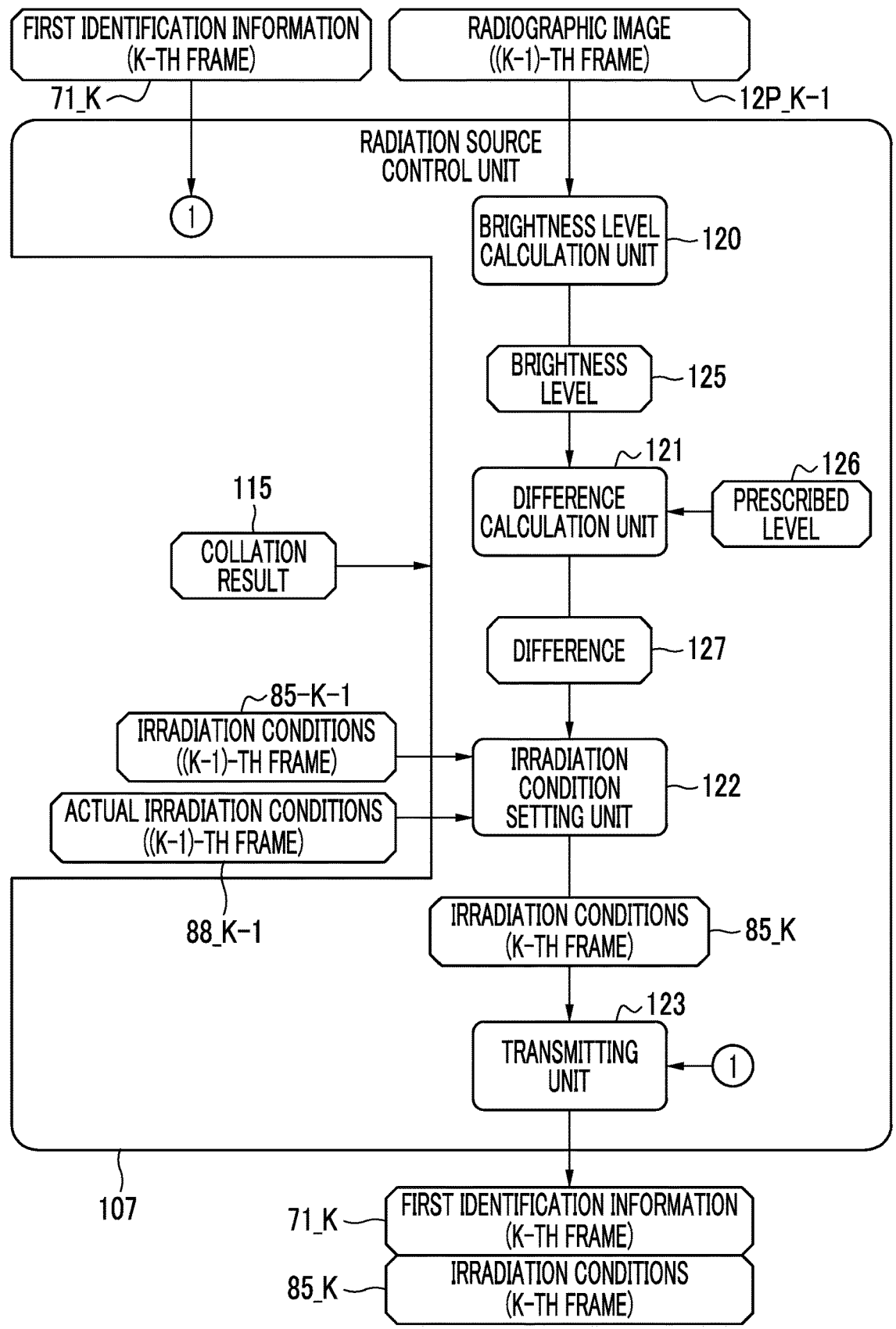
FIG. 15 is a block diagram illustrating a radiation source control unit.

In FIG. 15, in the case of the moving image capture, the radiation source control unit 107 functions as a brightness level calculation unit 120, a difference calculation unit 121, an irradiation condition setting unit 122, and a transmitting unit 123. The brightness level calculation unit 120 calculates a brightness level 125 of a radiographic image 12P_K−1 of a (K−1)-th frame subjected to image processing. The brightness level 125 is, for example, an average value of the pixel values of the radiographic image 12P_K−1. The brightness level calculation unit 120 outputs the brightness level 125 to the difference calculation unit 121. In addition, the brightness level 125 may be an average value of the pixel values except a region that is not irradiated with the radiation 10. The brightness level 125 is not limited to the average value and may be a median value.

The difference calculation unit 121 calculates a difference 127 between the brightness level 125 and a prescribed level 126. The difference calculation unit 121 outputs the difference 127 between the brightness level 125 and the prescribed level 126 to the irradiation condition setting unit 122. The prescribed level 126 is a target value of the brightness level 125 in the case of the irradiation conditions 85 which have been input by the radiology technician 13 through the operation input unit 45 and acquired by the irradiation condition acquisition unit 105. Therefore, in a case in which the brightness level 125 deviates from the prescribed level 126, it is necessary to perform automatic brightness control for updating the irradiation conditions 85 in order to set the brightness level 125 to the prescribed level 126.

The irradiation condition setting unit 122 sets the irradiation conditions 85 which have been input by the radiology technician 13 through the operation input unit 45 and acquired by the irradiation condition acquisition unit 105 in the first frame in the moving image capture. After the second frame, the irradiation condition setting unit 122 sets the irradiation conditions 85_K of the K-th frame on the basis of the irradiation conditions 85_K−1 of the (K−1)-th frame, the actual irradiation conditions 88_K−1 of the (K−1)-th frame, and the difference 127. The irradiation condition setting unit 122 outputs the irradiation conditions 85_K of the K-th frame to the transmitting unit 123. The irradiation conditions 85_K−1 of the (K−1)-th frame are the setting irradiation conditions set in the previous frame.

The transmitting unit 123 associates the first identification information 71_K with the irradiation conditions 85_K from the irradiation condition setting unit 122 and transmits them to the irradiation control device 42. Further, the transmitting unit 123 outputs the first identification information 71_K and the irradiation conditions 85_K to the RW control unit 113.

For example, the irradiation condition setting unit 122 calculates the tube voltage of the irradiation conditions 85_K of the K-th frame, using a relational expression in which the tube voltage of the irradiation conditions 85_K-1 of the (K-1)-th frame and the difference 127 between the brightness level 125 and the prescribed level 126 are parameters and the tube voltage of the irradiation conditions 85_K of the K-th frame is a solution. The outline of this relational expression is that, in a case in which the brightness level 125 is lower than the prescribed level 126, the tube voltage of the irradiation conditions 85_K of the K-th frame is increased from the tube voltage of the irradiation conditions 85_K-1 of the (K-1)-th frame and, in a case in which the brightness level 125 is higher than the prescribed level 126, the tube voltage of the irradiation conditions 85_K of the K-th frame is decreased from the tube voltage of the irradiation conditions 85_K-1 of the (K-1)-th frame. Instead of the relational expression, a data table in which the irradiation conditions 85_K-1 of the (K-1)-th frame and the irradiation conditions 85_K of the K-th frame corresponding to the difference 127 are registered may be used.

Further, the irradiation condition setting unit 122 calibrates the irradiation conditions 85_K of the K-th frame on the basis of the irradiation conditions 85_K-1 of the (K-1)-th frame and the actual irradiation conditions 88_K-1 of the (K-1)-th frame. That is, the irradiation condition setting unit 122 updates the irradiation conditions 85 on the basis of the actual irradiation conditions 88 in addition to the radiographic image 12. For example, a case is considered in which 50 kV is set as the tube voltage of the irradiation conditions 85_K-1 of the (K-1)-th frame and the tube voltage of the actual irradiation conditions 88_K-1 of the (K-1)-th frame is 40 kV due to a change in the performance of the radiation tube 28. In this case, 40 kV may be multiplied by 1.25 (=50/40) in order to actually emit the radiation 10 at the set tube voltage. Therefore, for example, in a case in which the tube voltage calculated by the relational expression is 100 kV, the irradiation condition setting unit 122 sets 125 kV (=100×1.25) as the final tube voltage of the irradiation conditions 85_K of the K-th frame. Here, the example in which the tube voltage of the irradiation conditions 85_K-1 of the (K-1)-th frame is updated has been described. However, the tube current and/or the irradiation time RT of the irradiation conditions 85_K-1 of the (K-1)-th frame may be updated in addition to or instead of the tube voltage.

Figure 16:
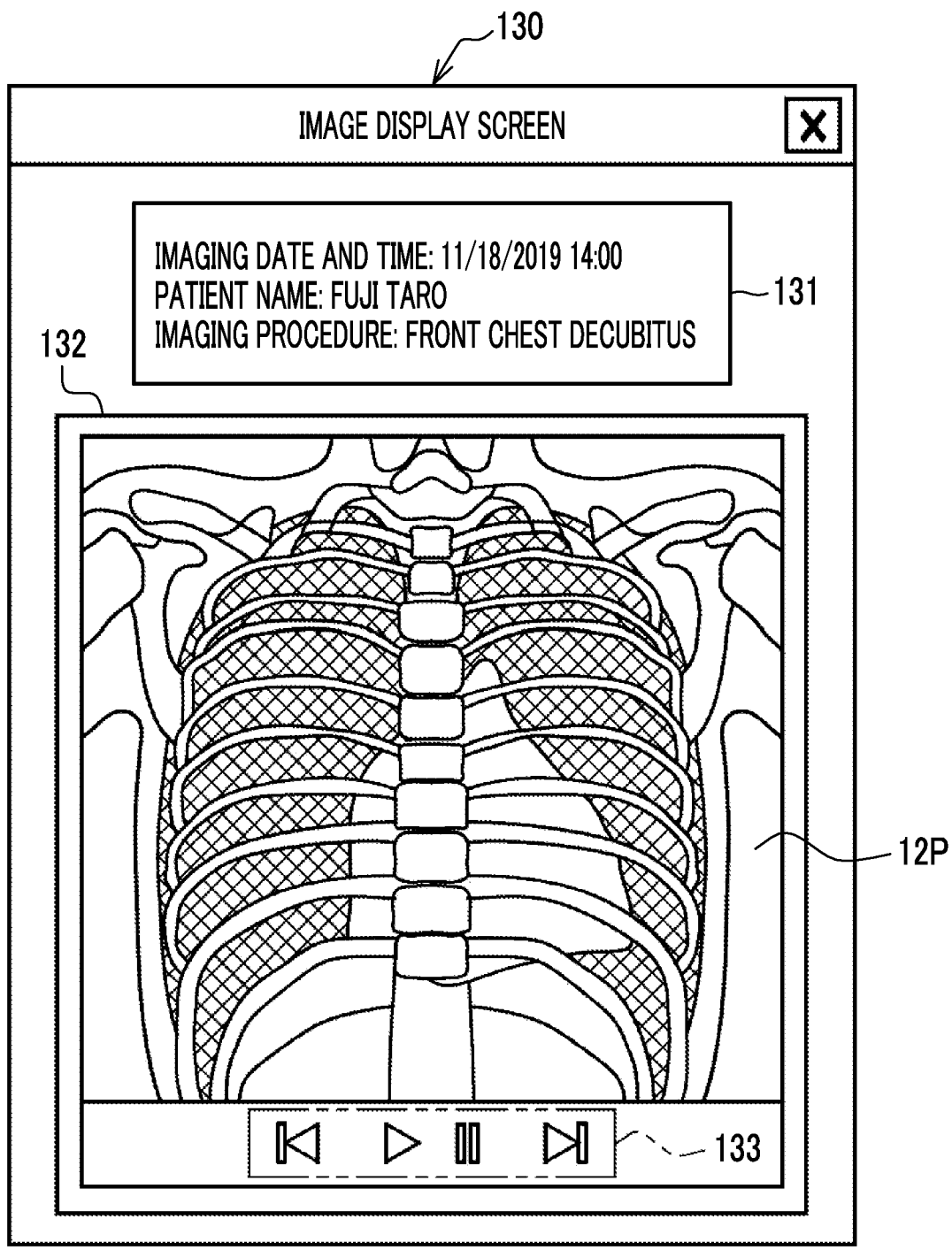
FIG. 16 is a diagram illustrating an image display screen.

In FIG. 16, an imaging information display frame 131 and an image display frame 132 are provided in the image display screen 130 displayed on the display 44 under the control of the display control unit 112. An imaging date and time, the name of the subject 11 (represented by a "patient name" in FIG. 16), and an imaging procedure are displayed in the imaging information display frame 131. The radiographic image 12P is displayed as a moving image in the image display frame 132.

An operation button group 133 is provided below the radiographic image 12P in the image display frame 132. The operation button group 133 includes a play button, a pause button, a frame return button, and a frame advance button for the display of the radiographic image 12P as a moving image.

Figure 17:
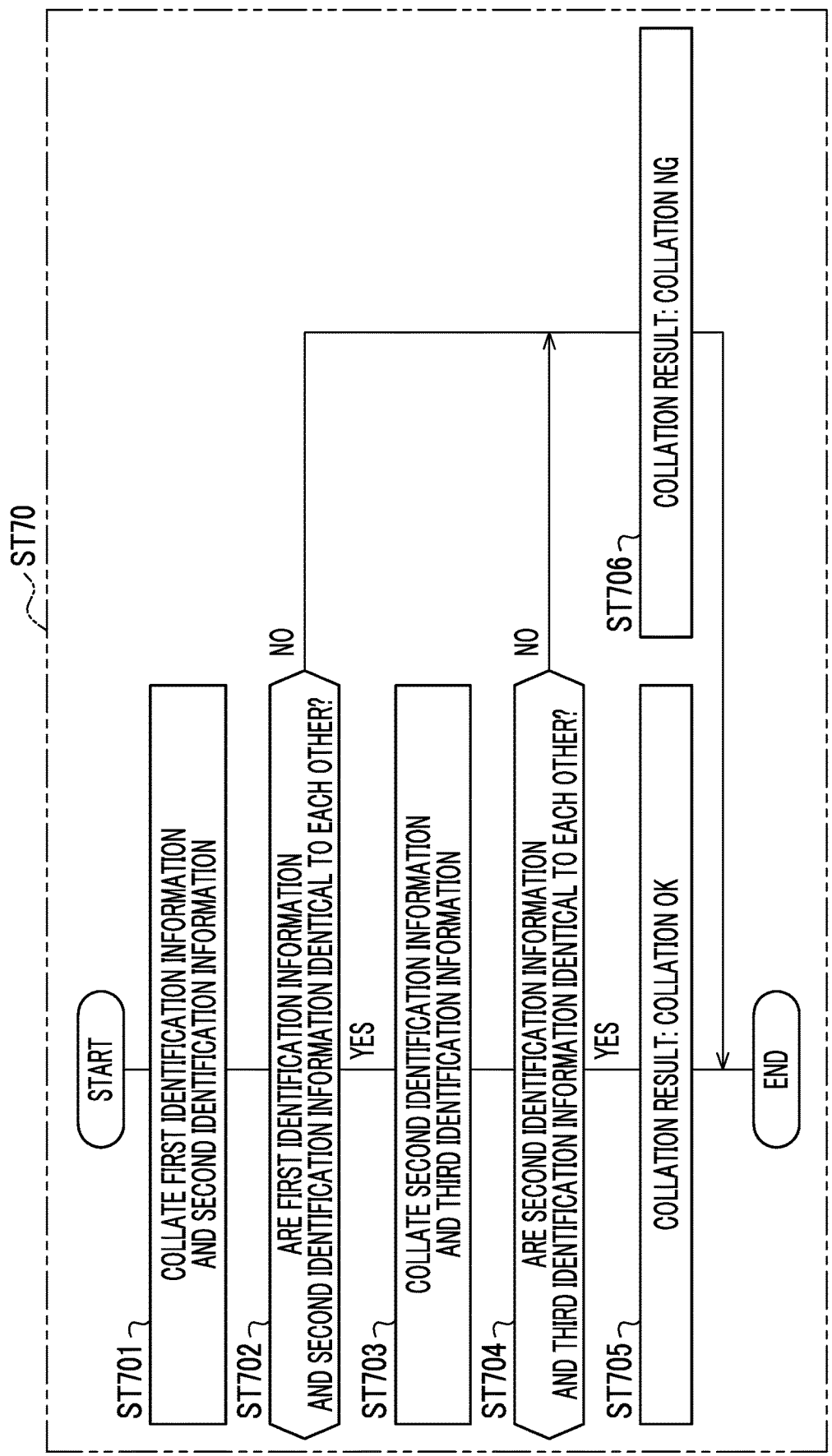
FIG. 17 is a flowchart illustrating a collation procedure of a collation unit.

As illustrated in FIG. 17, the collation unit 114 performs collation in the following procedure. First, the collation unit 114 collates the first identification information 71 and the second identification information 87 (Step ST701). In a case in which the first identification information 71 and the second identification information 87 are identical to each other (YES in Step ST702), the collation unit 114 collates the second identification information 87 and the third identification information 72 (Step ST703). In a case in which the second identification information 87 and the third identification information 72 are identical to each other (YES in Step ST704), the collation unit 114 outputs a collation result 115A (see FIG. 18A) indicating that collation is OK (Step ST705). Step ST701 is an example of a "collation step" according to the technology of the present disclosure.

In a case in which the first identification information 71 and the second identification information 87 are not identical to each other (NO in Step ST702), and in a case in which the second identification information 87 and the third identification information 72 are not identical to each other (NO in Step ST704), The collation unit 114 outputs a collation result 115B (see FIG. 18B) indicating that collation is NG (Step ST706).

The case in which the first identification information 71 and the second identification information 87 are identical to each other means that the irradiation with the radiation 10 has succeeded. On the contrary, the case in which the first identification information 71 and the second identification information 87 are not identical to each other means that the irradiation with the radiation 10 has failed. In a case in which the irradiation with the radiation 10 has failed, the second identification information 87 is carried over to the next frame, as illustrated in FIG. 13B. Therefore, the first identification information 71 and the second identification information 87 are not identical to each other.

Further, the case in which the second identification information 87 and the third identification information 72 are identical to each other means that the radiographic image 12 has been correctly transmitted. On the contrary, the case in which the second identification information 87 and the third identification information 72 are not identical to each other means that the radiographic image 12 has not been correctly transmitted. In a case in which the radiographic image 12 has not been correctly transmitted, the third identification information 72 is carried over to the next frame, as illustrated in FIG. 14B. Therefore, the second identification information 87 and the third identification information 72 are not identical to each other.

Figure 18:
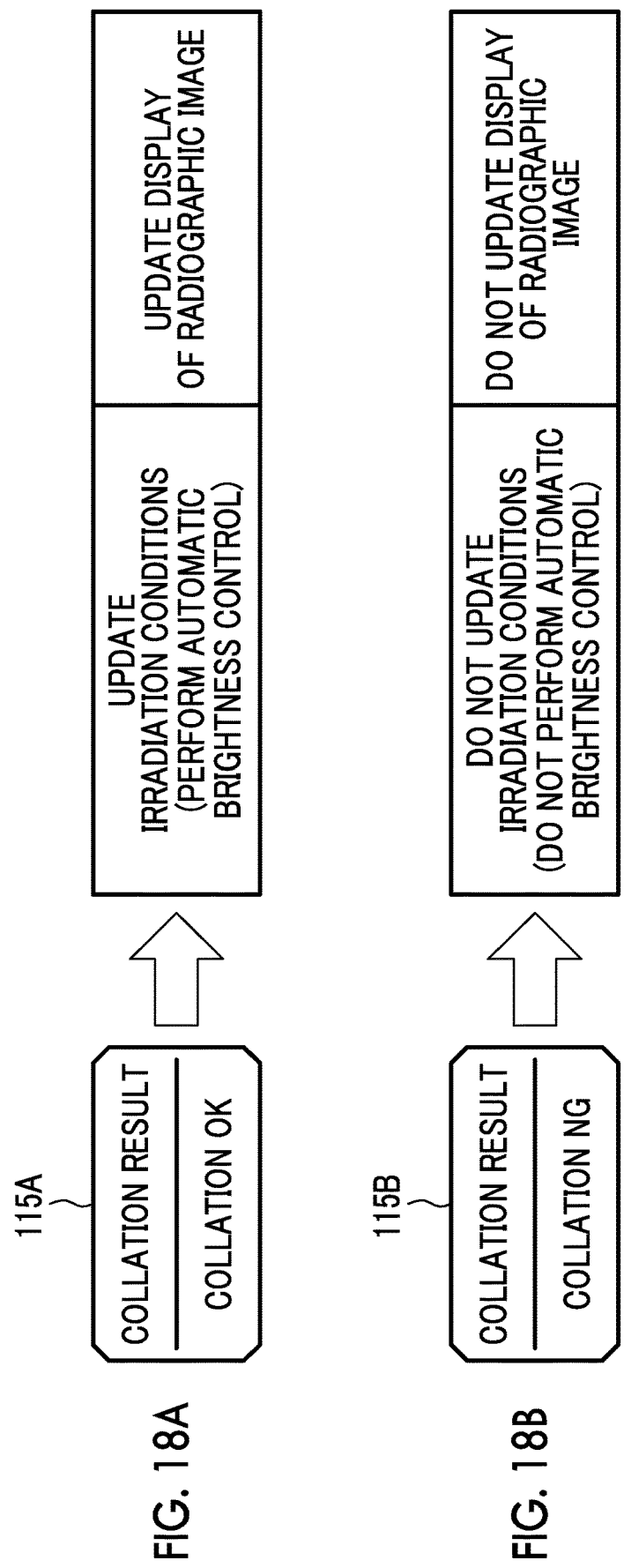
FIGS. 18A and 18B are diagrams illustrating an aspect of the update of the irradiation conditions and the update of the display of the radiographic image according to a collation result.

In FIGS. 18A and 18B, the radiation source control unit 107 determines whether or not to perform automatic brightness control according to the collation result 115. That is, the radiation source control unit 107 is an example of a "determination unit" according to the technology of the present disclosure. Specifically, in the case of the collation result 115A indicating that the collation is OK, the radiation source control unit 107 performs automatic brightness control to update the irradiation conditions 85_K-1 of the (K-1)-th frame to the irradiation conditions 85_K of the K-th frame as illustrated in FIG. 18A. Further, the display control unit 112 updates the display of the image display screen 130 using the radiographic image 12 received as a pair with the third identification information 72.

On the other hand, in the case of the collation result 115B indicating that the collation is NG the radiation source control unit 107 does not perform the automatic brightness control as illustrated in FIG. 18B. Further, the display control unit 112 does not update the display of the image display screen 130 using the radiographic image 12 received as a pair with the third identification information 72. In this case, the irradiation condition setting unit 122 uses the irradiation conditions 85 set in the previous frame. In addition, the display control unit 112 continuously displays the radiographic image 12 displayed in the previous frame on the image display screen 130.

Figure 19:
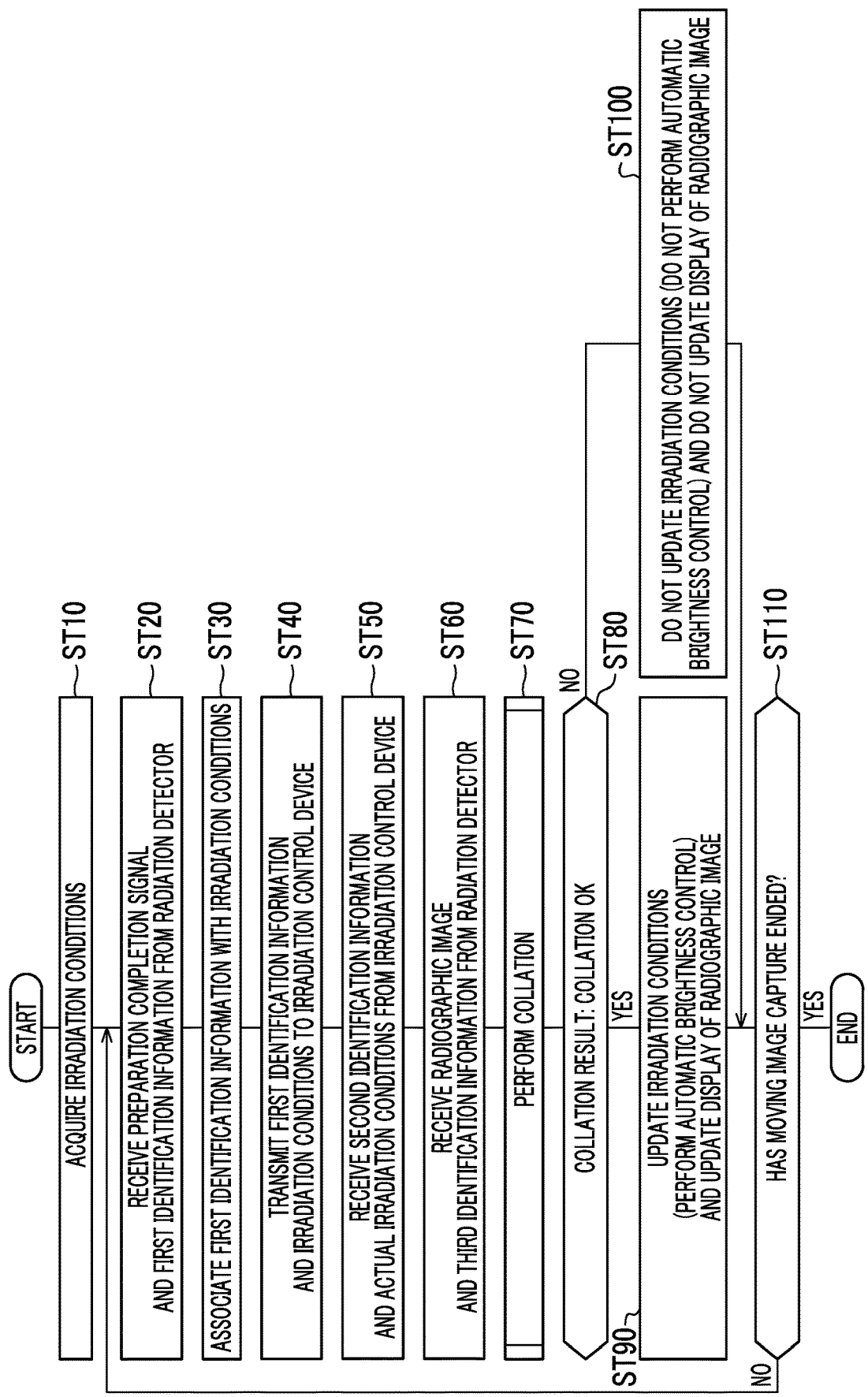
FIG. 19 is a flowchart illustrating a processing procedure of the imaging control device.
Figure 20:
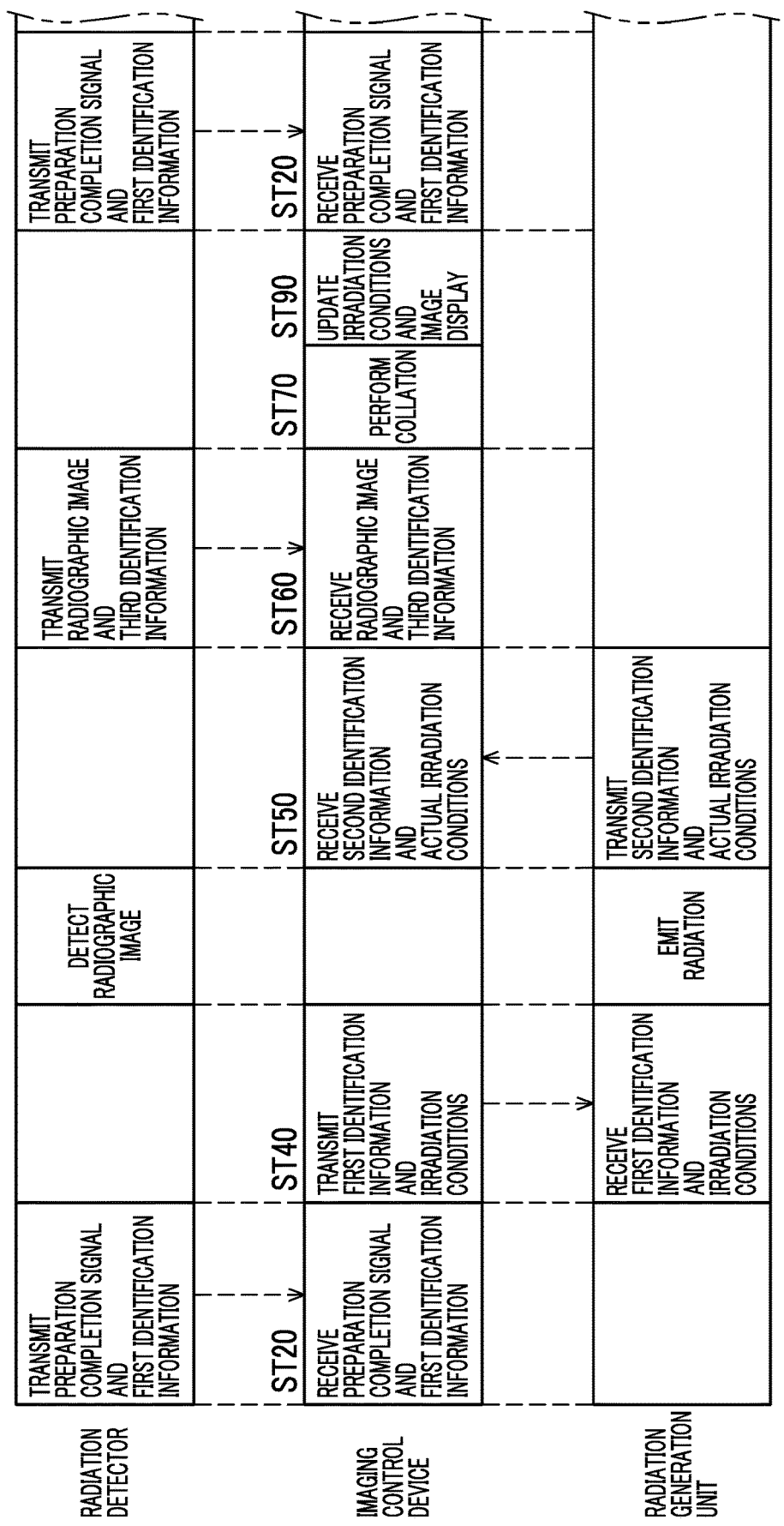
FIG. 20 is a timing chart illustrating a processing procedure of the radiation detector, the imaging control device, and the radiation generation unit.
Figure 21:
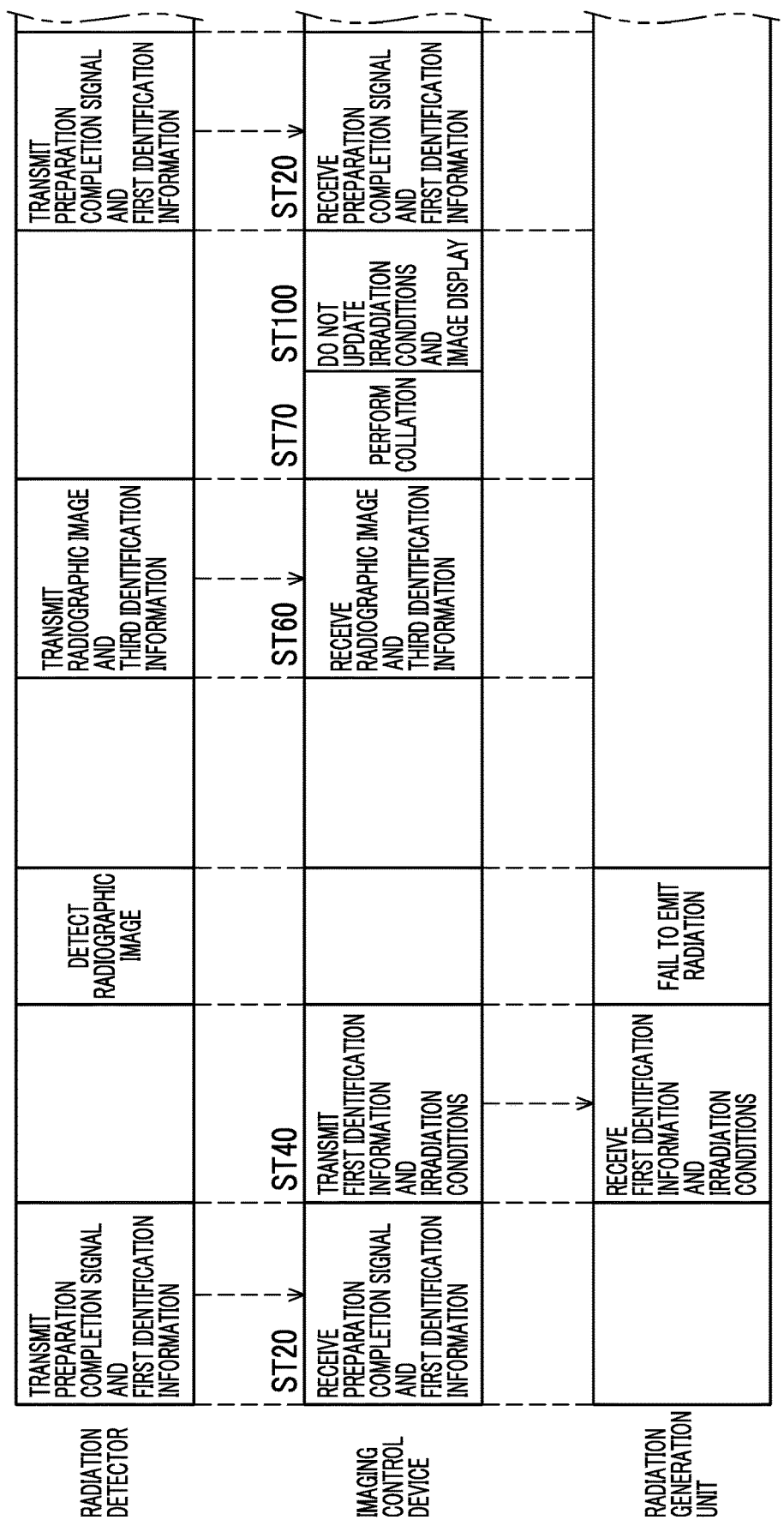
FIG. 21 is a timing chart illustrating a processing procedure of the radiation detector, the imaging control device, and the radiation generation unit in a case in which the irradiation with the radiation has failed.
Figure 22:
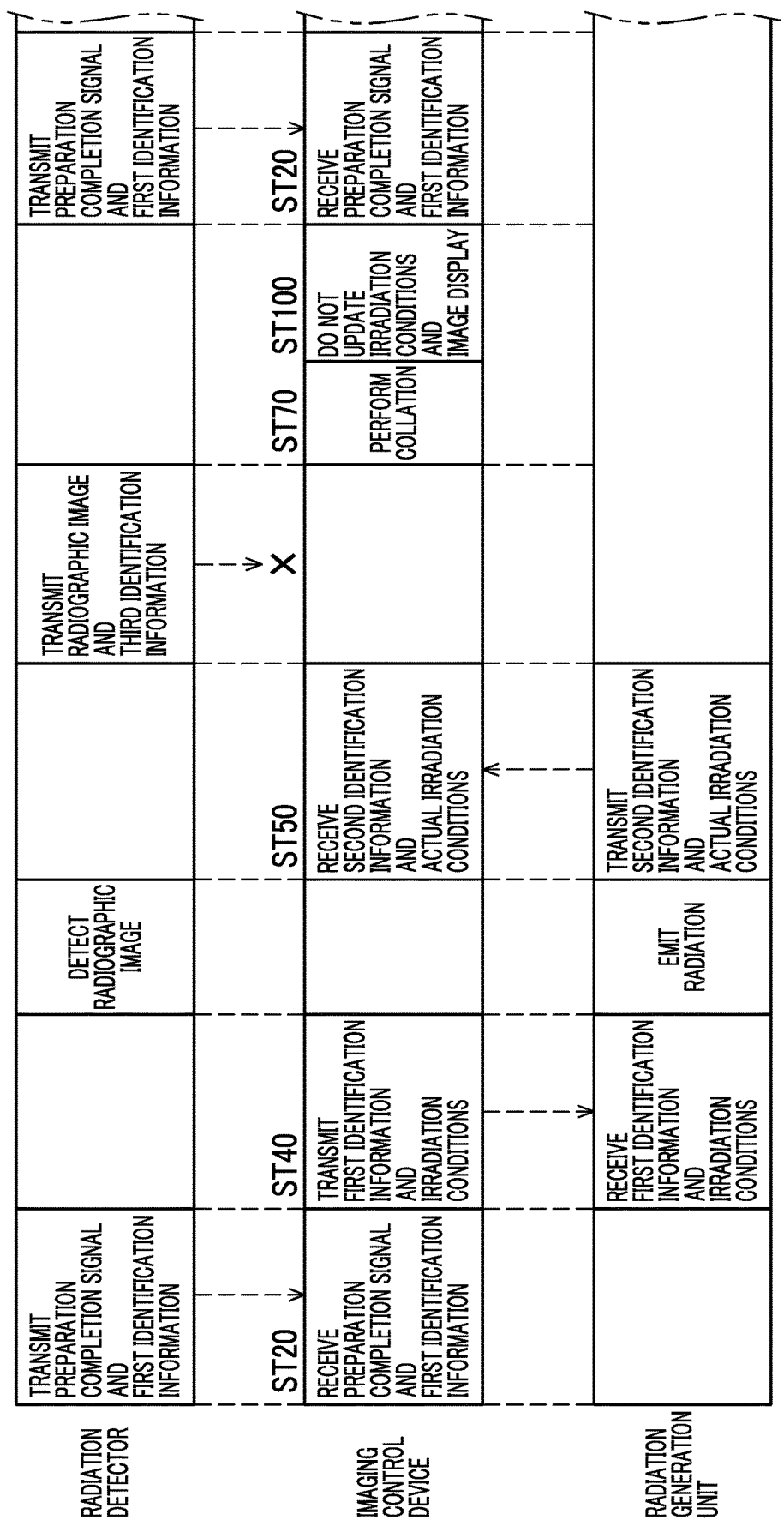
FIG. 22 is a timing chart illustrating a processing procedure of the radiation detector, the imaging control device, and the radiation generation unit in a case in which a communication failure occurs between the radiation detector and the imaging control device.

Next, the operation of the above configuration will be described with reference to a flowchart illustrated in FIG. 19 and timing charts illustrated in FIGS. 20 to 22. In a case in which the operation program 100 is started in the imaging control device 43, as illustrated in FIG. 12, the CPU 92 and the FPGA 93 of the imaging control device 43 function as the irradiation condition acquisition unit 105, the first receiving unit 106, the radiation source control unit 107, the detector control unit 108, the second receiving unit 109, the third receiving unit 110, the image processing unit 111, the display control unit 112, the RW control unit 113, and the collation unit 114.

First, the radiology technician 13 inputs the irradiation conditions 85 through the operation input unit 45 before the capture of a moving image. The irradiation conditions 85 are acquired by the irradiation condition acquisition unit 105 (Step ST10). The irradiation condition acquisition unit 105 outputs the irradiation conditions 85 to the radiation source control unit 107.

In a case in which the panel unit 52 is ready to receive the radiation 10, the radiation detector 25 transmits the preparation completion signal 70 and the first identification information 71 to the imaging control device 43. In the imaging control device 43, the first receiving unit 106 receives the preparation completion signal 70 and the first identification information 71 (Step ST20). The preparation completion signal 70 and the first identification information 71 are output from the first receiving unit 106 to the radiation source control unit 107. Step ST20 is an example of a "first receiving step" according to the technology of the present disclosure.

The radiation source control unit 107 associates the first identification information 71 with the irradiation conditions 85 (Step ST30). The radiation source control unit 107 transmits the first identification information 71 and the irradiation conditions 85 to the irradiation control device 42 (Step ST40). Further, the first identification information 71 and the irradiation conditions 85 are output from the radiation source control unit 107 to the RW control unit 113 and are stored in the storage device 90 by the RW control unit 113. Step ST40 is an example of a "transmitting step" according to the technology of the present disclosure.

In a case in which the radiology technician 13 inputs a command to start the capture of a moving image through the irradiation switch, the moving image capture illustrated in FIG. 6 is started under the set irradiation conditions 85. Specifically, the radiation 10 is intermittently emitted from the radiation source 26 a plurality of times under the control of the radiation source control unit 107. Further, the radiographic image 12 is output from the radiation detector 25 whenever the radiation 10 is emitted under the control of the detector control unit 108.

In a case in which the irradiation with the radiation 10 has succeeded, the irradiation control device 42 transmits the second identification information 87 and the actual irradiation conditions 88 to the imaging control device 43. In the imaging control device 43, the second receiving unit 109 receives the second identification information 87 and the actual irradiation conditions 88 (Step ST50). The second identification information 87 and the actual irradiation conditions 88 are output from the second receiving unit 109 to the RW control unit 113 and are stored in the storage device 90 by the RW control unit 113. Step ST50 is an example of a "second receiving step" according to the technology of the present disclosure. In a case in which the irradiation with the radiation 10 has failed, the irradiation control device 42 does not transmit the second identification information 87 and the actual irradiation conditions 88 to the imaging control device 43. Therefore, Step ST50 is omitted as illustrated in FIG. 21.

In a case in which the communication between the radiation detector 25 and the imaging control device 43 is good, the radiographic image 12 and the third identification information 72 are transmitted from the radiation detector 25 to the imaging control device 43. In the imaging control device 43, the third receiving unit 110 receives the radiographic image 12 and the third identification information 72 (Step ST60). The radiographic image 12 is output from the third receiving unit 110 to the image processing unit 111 and is subjected to various types of image processing by the image processing unit 111 to become the radiographic image 12P subjected to the image processing. The radiographic image 12P subjected to the image processing is output from the image processing unit 111 to the RW control unit 113 and is stored in the storage device 90 by the RW control unit 113. In addition, the third identification information 72 is output from the third receiving unit 110 to the RW control unit 113 and is stored in the storage device 90 by the RW control unit 113. In a case in which a communication failure occurs between the radiation detector 25 and the imaging control device 43, the radiographic image 12 and the third identification information 72 are not transmitted from the radiation detector 25 to the imaging control device 43. Therefore, Step ST60 is omitted as illustrated in FIG. 22.

The RW control unit 113 reads the first identification information 71, the second identification information 87, and the third identification information 72 from the storage device 90 and outputs them to the collation unit 114. Then, the collation unit 114 collates the first identification information 71, the second identification information 87, and the third identification information 72 as illustrated in FIG. 17 (Step ST70).

In the case of the collation result 115A indicating the collation is OK (YES in Step ST80), as illustrated in FIG. 18A, the radiation source control unit 107 performs the automatic brightness control for updating the irradiation conditions 85. In this case, as illustrated in FIG. 15, the irradiation condition setting unit 122 updates the irradiation conditions 85 on the basis of the brightness level 125 and the actual irradiation conditions 88 of the radiographic image 12P. Further, the display control unit 112 updates the display of the radiographic image 12P on the image display screen 130 (Step ST90). Step ST90 is an example of a "determination step" according to the technology of the present disclosure.

In contrast, in the case of the collation result 115B indicating the collation is NG (NO in Step ST80), the automatic brightness control is not performed as illustrated in FIG. 18B. Further, the display of the radiographic image 12P on the image display screen 130 is not updated (Step ST100). Similar to Step ST90, Step ST100 is an example of the "determination step" according to the technology of the present disclosure. The process in ST20 to ST90 or ST20 to ST100 is repeated as long as the moving image capture does not end (NO in Step ST110).

As described above, the CPU 92 and the FPGA 93 of the imaging control device 43 receive the preparation completion signal 70 and the first identification information 71 from the radiation detector 25 and transmit the first identification information 71 and the irradiation conditions 85 of the radiation 10 associated with the first identification information 71 to the radiation generation unit 46. Then, the CPU 92 and the FPGA 93 receive, from the radiation generation unit 46, the second identification information 87 copied from the first identification information 71 by the radiation generation unit 46 in a case in which the irradiation with the radiation 10 has succeeded. Then, the CPU 92 and the FPGA 93 collate the first identification information 71 and the second identification information 87 and determine whether or not to perform the automatic brightness control on the basis of the collation result 115. Therefore, it is possible to suppress inappropriate automatic brightness control.

The CPU 92 and the FPGA 93 do not perform the automatic brightness control in a case in which the first identification information 71 and the second identification information 87 are not identical to each other. Therefore, the irradiation conditions are not updated by mistake on the basis of the radiographic image 12 obtained in a case in which the irradiation with the radiation 10 has failed.

The radiation generation unit 46 detects the actual irradiation conditions 88 and associates the actual irradiation conditions 88 with the second identification information 87. The CPU 92 and the FPGA 93 receive the actual irradiation conditions 88 from the radiation generation unit 46 in addition to the second identification information 87. Then, in a case in which the automatic brightness control is performed, the irradiation conditions 85 are updated on the basis of the actual irradiation conditions 88 in addition to the radiographic image 12. Therefore, it is possible to set the irradiation conditions 85 adapted to a change in the performance of the radiation tube 28.

The CPU 92 and the FPGA 93 perform control to display the radiographic image 12 according to the frame interval FI. Then, in a case in which the first identification information 71 and the second identification information 87 are not identical to each other, the display of the radiographic image 12 is not updated. Therefore, it is possible to prevent the user from feeling uncomfortable due to the display of the radiographic image 12 that has been obtained in a case in which the irradiation with the radiation 10 has failed and is meaningless as data.

The CPU 92 and the FPGA 93 receive the radiographic image 12 and the third identification information 72 from the radiation detector 25. Then, the first identification information 71 and the second identification information 87 are collated. In a case in which the first identification information 71 and the second identification information 87 are identical to each other, the second identification information 87 and the third identification information 72 are collated. Therefore, it is possible to know not only whether or not the irradiation with the radiation 10 fails but also whether or not a communication failure occurs between the radiation detector 25 and the imaging control device 43.

The CPU 92 and the FPGA 93 perform the automatic brightness control only in a case in which the first identification information 71 and the second identification information 87 are identical to each other and the second identification information 87 and the third identification information 72 are identical to each other. Therefore, it is possible to prevent the irradiation conditions from being updated by mistake on the basis of the radiographic image 12 obtained in a case in which the irradiation with the radiation 10 has failed and to prevent the irradiation conditions from being updated by mistake on the basis of the radiographic image 12 that is not correctly transmitted due to the communication failure between the radiation detector 25 and the imaging control device 43. As a result, it is possible to further improve the accuracy of the automatic brightness control.

The CPU 92 and the FPGA 93 update the display of the radiographic image 12 only in a case in which the first identification information 71 and the second identification information 87 are identical to each other and the second identification information 87 and the third identification information 72 are identical to each other. Therefore, it is possible to prevent the undesirable radiographic images 12, such as the radiographic image 12 that has been obtained in a case in which the irradiation with the radiation 10 has failed and is meaningless as data and the radiographic image 12 that is not transmitted correctly, from being displayed to the eyes of the user.

The radiation detector 25 is removable as illustrated in FIG. 2. In this case, there is a relatively high probability that a communication failure will occur due to, for example, the bad accommodation posture of the radiation detector 25 in the holder 27, a contact failure in a contact for wire communication, and the deterioration of a contact caused by repeated attachment and detachment. Therefore, it can be said that the usefulness of the effect of knowing whether or not a communication failure occurs between the radiation detector 25 and the imaging control device 43 using the collation between the second identification information 87 and the third identification information 72 is higher than that in a case in which the radiation detector 25 is not removable.

In addition, the imaging control device 43 may perform the offset correction process, the sensitivity correction process, and the defective pixel correction process performed by the correction processing circuit 62 of the radiation detector 25.

The following method may be adopted as a method for calibrating the irradiation conditions 85_K of the K-th frame on the basis of the irradiation conditions 85_K−1 of the (K−1)-th frame and the actual irradiation conditions 88_K−1 of the (K−1)-th frame. That is, the actual irradiation conditions 88_K−1 for the (K−1)-th frame is transmitted from the irradiation control device 42 to the imaging control device 43 at a predetermined timing such as at the start of work. Then, a calibration coefficient, by which the tube voltage or the like of the irradiation conditions 85_K of the K-th frame is to be multiplied, is calculated on the basis of the irradiation conditions 85_K−1 of the (K−1)-th frame and the actual irradiation conditions 88_K−1 of the (K−1)-th frame. The calculated calibration coefficient is stored in the storage device 90. In a case in which the irradiation condition setting unit 122 sets the irradiation conditions 85_K of the K-th frame, the calibration coefficient is read from the storage device 90 and is then used. Therefore, it is possible to reduce the time and effort required to calculate the calibration coefficient for each frame.

The automatic brightness control may not be performed for each frame in the moving image capture. For example, the automatic brightness control may be performed only for even-numbered frames. Further, the automatic brightness control may be performed only for the first few frames.

In this embodiment, the third identification information 72 is received, and the second identification information 87 and the third identification information 72 are collated. However, the technology of the present disclosure also includes an aspect in which this process is not performed and only the collation between the first identification information 71 and the second identification information 87 is performed.

The hardware configuration of the computer forming the imaging control device 43 can be modified in various ways. For example, the imaging control device 43 may be configured by a plurality of computers separated as hardware in order to improve processing capability and reliability. Specifically, the functions of the irradiation condition acquisition unit 105, the display control unit 112, and the RW control unit 113 and the functions of the first receiving unit 106, the radiation source control unit 107, the detector control unit 108, the second receiving unit 109, the third receiving unit 110, the image processing unit 111 and the collation unit 114 are distributed to two computers. In this case, the two computers form the imaging control device 43.

As such, the hardware configuration of the computer of the imaging control device 43 can be appropriately changed according to required performances, such as processing capacity, safety, and reliability. Further, not only the hardware but also an application program, such as the operation program 100, may be duplicated or may be dispersively stored in a plurality of storage devices in order to ensure safety and reliability.

In each of the above-described embodiments, for example, the following various processors can be used as a hardware structure of processing units performing various processes, such as the irradiation condition acquisition unit 105, the first receiving unit 106, the radiation source control unit 107, the detector control unit 108, the second receiving unit 109, the third receiving unit 110, the image processing unit 111, the display control unit 112, the RW control unit 113, the collation unit 114, the brightness level calculation unit 120, the difference calculation unit 121, the irradiation condition setting unit 122, and the transmitting unit 123. The various processors include, for example, the CPU 92 which is a general-purpose processor executing software to function as various processing units, a PLD, such as the FPGA 93, and a dedicated electric circuit, such as an ASIC.

One processing unit may be configured by one of the various processors or a combination of two or more processors of the same type or different types (for example, a combination of a plurality of FPGAs and a combination of a CPU and an FPGA). Further, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system on chip (SoC). As such, various processing units are configured by using one or more of the various processors as the hardware structure.

In addition, specifically, an electric circuit (circuitry) obtained by combining circuit elements, such as semiconductor elements, can be used as the hardware structure of the various processors.

The technology of the present disclosure may be appropriately combined with the above-described various embodiments and various modification examples. Further, it is needless to say that the present disclosure is not limited to each of the above-described embodiments and various configurations can be adopted without departing from the scope of the invention. Furthermore, the technology of the present disclosure extends to a storage medium that non-temporarily stores a program, in addition to the program.

The above descriptions and illustrations are detailed descriptions of portions related to the technology of the present disclosure and are merely examples of the technology of the present disclosure. For example, the above description of the configurations, functions, operations, and effects is the description of examples of the configurations, functions, operations, and effects of portions according to the technology of the present disclosure. Therefore, unnecessary portions may be deleted or new elements may be added or replaced in the above descriptions and illustrations without departing from the scope and spirit of the technology of the present disclosure. In addition, the description of, for example, common technical knowledge that does not need to be particularly described to enable the implementation of the technology of the present disclosure is omitted in order to avoid confusion and to facilitate the understanding of portions related to the technology of the present disclosure.

In the specification, "A and/or B" is synonymous with "at least one of A or B". That is, "A and/or B" means only A, only B, or a combination of A and B. Further, in the specification, the same concept as "A and/or B" is applied to a case in which the connection of three or more matters is expressed by "and/or".

All of the documents, the patent applications, and the technical standards described in the specification are incorporated by reference herein to the same extent as each individual document, each patent application, and each technical standard are specifically and individually stated to be incorporated by reference.

What is claimed is:

1. An imaging control device that controls radiographic moving image capture which irradiates a subject with radiation from a radiation generation unit including a radiation source and outputs a radiographic image output from a radiation detector at a predetermined frame interval, the imaging control device comprising:

at least one processor, wherein the processor receives first identification information and a preparation completion signal indicating that preparation for receiving the radiation has been completed from the radiation detector, transmits the first identification information and irradiation conditions of the radiation associated with the first identification information to the radiation generation unit, receives, from the radiation generation unit, second identification information copied from the first identification information by the radiation generation unit in a case in which the irradiation with the radiation has succeeded, collates the first identification information and the second identification information, and determines whether or not to perform automatic brightness control, which sets a brightness level of the radiographic image to a prescribed level and updates the irradiation conditions on the basis of the radiographic image, according to a collation result.

2. The imaging control device according to claim 1, wherein the processor does not perform the automatic brightness control in a case in which the first identification information and the second identification information are not identical to each other.

3. The imaging control device according to claim 1, wherein the radiation generation unit detects actual irradiation conditions which are actual irradiation conditions of the radiation and associates the actual irradiation conditions with the second identification information, and the processor receives the actual irradiation conditions from the radiation generation unit in addition to the second identification information, and updates the irradiation conditions on the basis of the actual irradiation conditions in addition to the radiographic image in a case in which the automatic brightness control is performed.

4. The imaging control device according to claim 1, wherein the processor performs control to display the radiographic image at the frame interval, and does not update the display of the radiographic image in a case in which the first identification information and the second identification information are not identical to each other.

5. The imaging control device according to claim 1, wherein the processor receives, from the radiation detector, the radiographic image output from the radiation detector on the basis of the radiation emitted from the radiation generation unit under the irradiation conditions and third identification information which is copied from the first identification information and is associated with the radiographic image by the radiation detector, collates the first identification information and the second identification information, and collates the second identification information and the third identification information in a case in which the first identification information and the second identification information are identical to each other.

6. The imaging control device according to claim 5, wherein the processor performs the automatic brightness control only in a case in which the first identification information and the second identification information are identical to each other and the second identification information and the third identification information are identical to each other.

7. The imaging control device according to claim 5, wherein the processor performs control to display the radiographic image according to the frame interval, and updates the display of the radiographic image only in a case in which the first identification information and the second identification information are identical to each other and the second identification information and the third identification information are identical to each other.

8. The imaging control device according to claim 5, wherein the imaging control device is used in a radiography apparatus including the radiation detector that is removable.

9. A method for operating an imaging control device that controls radiographic moving image capture which irradiates a subject with radiation from a radiation generation unit including a radiation source and outputs a radiographic image output from a radiation detector at a predetermined frame interval, the method comprising:

a first receiving step of receiving first identification information and a preparation completion signal indicating that preparation for receiving the radiation has been completed from the radiation detector;

a transmitting step of transmitting the first identification information and irradiation conditions of the radiation associated with the first identification information to the radiation generation unit;

a second receiving step of receiving, from the radiation generation unit, second identification information copied from the first identification information by the radiation generation unit in a case in which the irradiation with the radiation has succeeded;

a collation step of collating the first identification information and the second identification information; and a determination step of determining whether or not to perform automatic brightness control, which sets a brightness level of the radiographic image to a prescribed level and updates the irradiation conditions on the basis of the radiographic image, according to a collation result.

10. A non-transitory computer-readable storage medium storing a program for operating an imaging control device that controls radiographic moving image capture which irradiates a subject with radiation from a radiation generation unit including a radiation source and outputs a radiographic image output from a radiation detector at a predetermined frame interval, the program causing a computer to function as:

a first receiving unit that receives first identification information and a preparation completion signal indicating that preparation for receiving the radiation has been completed from the radiation detector;

a transmitting unit that transmits the first identification information and irradiation conditions of the radiation associated with the first identification information to the radiation generation unit;

a second receiving unit that receives, from the radiation generation unit, second identification information copied from the first identification information by the radiation generation unit in a case in which the irradiation with the radiation has succeeded;

a collation unit that collates the first identification information and the second identification information; and a determination unit that determines whether or not to perform automatic brightness control, which sets a brightness level of the radiographic image to a prescribed level and updates the irradiation conditions on the basis of the radiographic image, according to a collation result.

11. A radiography apparatus comprising:

a radiation generation unit including a radiation source that irradiates a subject with radiation;

a radiation detector that receives the radiation transmitted through the subject and outputs a radiographic image; and an imaging control device that controls radiographic moving image capture which outputs the radiographic image output from the radiation detector at a predetermined frame interval, wherein the radiation detector transmits first identification information and a preparation completion signal indicating that preparation for receiving the radiation has been completed to the imaging control device, the imaging control device transmits the first identification information and irradiation conditions of the radiation associated with the first identification information to the radiation generation unit, the radiation generation unit transmits, to the imaging control device, second identification information copied from the first identification information in a case in which the irradiation with the radiation has succeeded, and the imaging control device collates the first identification information and the second identification information, and determines whether or not to perform automatic brightness control, which sets a brightness level of the radiographic image to a prescribed level and updates the irradiation conditions on the basis of the radiographic image, according to a collation result.

* * * * *